United States Patent
Kelley et al.

(10) Patent No.: US 10,434,316 B2
(45) Date of Patent: Oct. 8, 2019

(54) FLEXIBLE RECHARGEABLE IMPLANTABLE SUBCUTANEOUS MEDICAL DEVICE STRUCTURE AND METHOD OF ASSEMBLY

(71) Applicant: NewPace Ltd., Caesarea (IL)

(72) Inventors: James Kelley, Coon Rapids, MN (US); Jack Amir, Mazkeret Batya (IL); Moty Mocha, Beit Dagan (IL); Gera Strommer, Haifa (IL); Avraham Broder, Petach Tikva (IL); Robert Fishel, Delray Beach, FL (US)

(73) Assignee: NewPace Ltd., Caesarea (IL)

( * ) Notice: Subject to any disclaimer, the term of this patent is extended or adjusted under 35 U.S.C. 154(b) by 0 days.

(21) Appl. No.: 15/509,405

(22) PCT Filed: Sep. 6, 2015

(86) PCT No.: PCT/IL2015/050895
§ 371 (c)(1),
(2) Date: Mar. 7, 2017

(87) PCT Pub. No.: WO2016/038599
PCT Pub. Date: Mar. 17, 2016

(65) Prior Publication Data
US 2017/0246459 A1    Aug. 31, 2017

Related U.S. Application Data

(60) Provisional application No. 62/047,081, filed on Sep. 8, 2014.

(51) Int. Cl.
*A61N 1/00*  (2006.01)
*A61N 1/365*  (2006.01)
(Continued)

(52) U.S. Cl.
CPC ....... *A61N 1/36542* (2013.01); *A61N 1/0568* (2013.01); *A61N 1/08* (2013.01);
(Continued)

(58) Field of Classification Search
CPC ............... A61N 1/375; A61N 1/37512; A61N 1/3752–3758; A61N 1/3956; A61N 1/3968; A61N 1/0504; A61N 1/0587
See application file for complete search history.

(56) References Cited

U.S. PATENT DOCUMENTS 5,133,353 A    7/1992   Hauser
5,261,400 A   11/1993   Bardy
(Continued)

FOREIGN PATENT DOCUMENTS

CN    101115525 A    1/2008
EP      1631350 A2    3/2006
(Continued)

OTHER PUBLICATIONS

International Search Report and Written Opinion of the International Searching Authority dated Feb. 4, 2014 for International Application No. PCT/US2013/071338 (12 Pages).
(Continued)

*Primary Examiner* — Scott M. Getzow
(74) *Attorney, Agent, or Firm* — Brown Rudnick LLP

(57) ABSTRACT

Flexible implantable subcutaneous heart device (HD) structure, including a flexible device body, at least one flexible lead and at least one respective transition unit, the transition unit for respectively coupling each flexible lead to the flexible device body, the flexible device body including a plurality of inner components and a respective plurality of hollow outer units, the hollow outer units for encasing and protecting the inner components, each one of the hollow outer units including at least one hollow rigid element and a hollow flexible element, the hollow flexible element coupled with the hollow rigid element for enabling the outer unit a degree of flexibility, wherein the hollow flexible element is covered with a covering and wherein the flexible device body is covered with a polymer.

36 Claims, 14 Drawing Sheets

(51) Int. Cl.
*A61N 1/375* (2006.01)
*A61N 1/05* (2006.01)
*A61N 1/08* (2006.01)
*A61N 1/39* (2006.01)

(52) U.S. Cl.
CPC .......... *A61N 1/375* (2013.01); *A61N 1/3956* (2013.01); *A61N 1/0504* (2013.01); *A61N 1/3756* (2013.01)

(56) References Cited

U.S. PATENT DOCUMENTS

| | | | |
|---|---|---|---|
| 5,314,451 A | 5/1994 | Mulier | |
| 5,333,095 A * | 7/1994 | Stevenson | A61N 1/3754 29/25.42 |
| 5,480,416 A * | 1/1996 | Garcia | A61N 1/05 607/116 |
| 5,573,551 A | 11/1996 | Lin et al. | |
| 5,645,586 A | 7/1997 | Meltzer | |
| 6,256,541 B1 | 7/2001 | Heil et al. | |
| 6,647,292 B1 | 11/2003 | Bardy et al. | |
| 6,721,597 B1 | 4/2004 | Bardy et al. | |
| 7,069,075 B2 | 6/2006 | Olson | |
| 7,363,083 B2 | 4/2008 | Bardy et al. | |
| 7,617,007 B2 | 11/2009 | Williams et al. | |
| 7,684,864 B2 | 3/2010 | Olson et al. | |
| 7,835,790 B2 | 11/2010 | Ostroff et al. | |
| 7,894,894 B2 | 2/2011 | Stadler et al. | |
| 7,894,915 B1 | 2/2011 | Chitre et al. | |
| 7,899,554 B2 | 3/2011 | Williams et al. | |
| 7,937,148 B2 | 5/2011 | Jacobson | |
| 8,135,459 B2 | 3/2012 | Bardy et al. | |
| 8,147,486 B2 | 4/2012 | Honour et al. | |
| 8,260,415 B2 | 9/2012 | Donofrio | |
| 8,311,633 B2 | 11/2012 | Ransbury et al. | |
| 8,359,094 B2 | 1/2013 | Bonner et al. | |
| 8,483,841 B2 | 7/2013 | Sanghera et al. | |
| 8,512,254 B2 | 8/2013 | Donofrio | |
| 8,644,926 B2 | 2/2014 | Ostroff et al. | |
| 8,718,760 B2 | 5/2014 | Bardy et al. | |
| 8,768,458 B2 | 7/2014 | Bardy et al. | |
| 2002/0082658 A1 * | 6/2002 | Heinrich | A61N 1/3622 607/9 |
| 2003/0045892 A1 | 3/2003 | Kaladelfos | |
| 2004/0176818 A1 | 9/2004 | Wahlstrand et al. | |
| 2004/0210292 A1 | 10/2004 | Bardy et al. | |
| 2005/0043765 A1 | 2/2005 | Williams et al. | |
| 2006/0247688 A1 | 11/2006 | Olson et al. | |
| 2007/0038052 A1 * | 2/2007 | Swoyer | A61N 1/0551 600/345 |
| 2008/0000882 A1 * | 1/2008 | VanDerlick | A61N 1/375 219/121.64 |
| 2008/0167702 A1 | 7/2008 | Ransbury et al. | |
| 2008/0183230 A1 | 7/2008 | Kemmetmueller et al. | |
| 2008/0249591 A1 * | 10/2008 | Gaw | A61N 1/37235 607/60 |
| 2008/0294210 A1 | 11/2008 | Rosero | |
| 2009/0076401 A1 | 3/2009 | Mazar et al. | |
| 2009/0149902 A1 | 6/2009 | Kumar et al. | |
| 2009/0192381 A1 | 7/2009 | Brockway et al. | |
| 2010/0049318 A1 * | 2/2010 | Jolly | A61B 5/6882 623/10 |
| 2010/0228306 A1 * | 9/2010 | Bardy | A61N 1/375 607/5 |
| 2013/0184796 A1 * | 7/2013 | Marzano | A61N 1/3754 607/116 |
| 2018/0070876 A1 * | 3/2018 | Brockway | A61B 5/686 |

FOREIGN PATENT DOCUMENTS

| | | |
|---|---|---|
| EP | 2510973 A2 | 10/2012 |
| WO | 2003/002198 A2 | 1/2003 |
| WO | 2004/028628 A1 | 4/2004 |
| WO | 2004/108212 A2 | 12/2004 |
| WO | 2007103262 A2 | 9/2007 |
| WO | 2012/013360 A1 | 2/2012 |
| WO | 2014/081978 A1 | 5/2014 |

OTHER PUBLICATIONS

First Office Action of State Intellectual Property Office dated Feb. 25, 2016, for Chinese Patent Application No. 2013800690053 (19 Pages).

Extended European Search Report dated Jul. 25, 2007 for European Patent Application No. 13857150.0 (9 Pages).

International Search Report and Written Opinion of the International Searching Authority dated Jan. 7, 2016 for International Application No. PCT/IL2015/050895 (11 Pages).

Bardy, 2010, N. Engl. J. Med. 363(1):36-44.

Extended European Search Report dated May 15, 2018 for EP 15839301.7 (6 pages).

\* cited by examiner

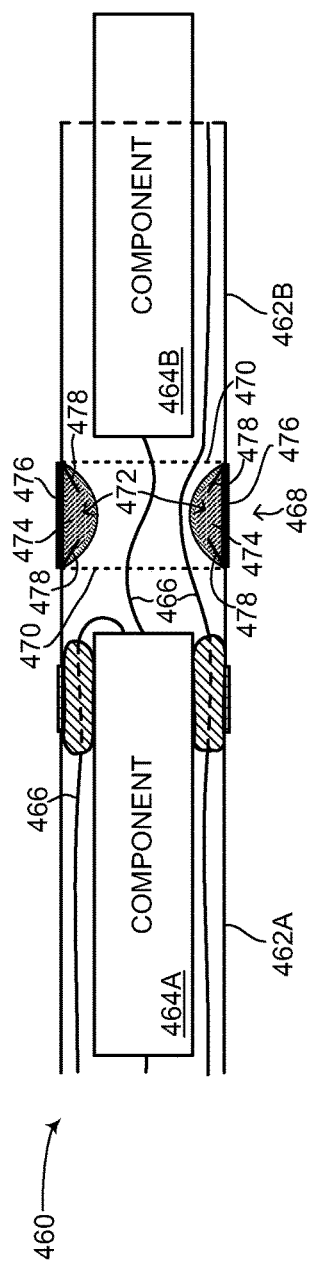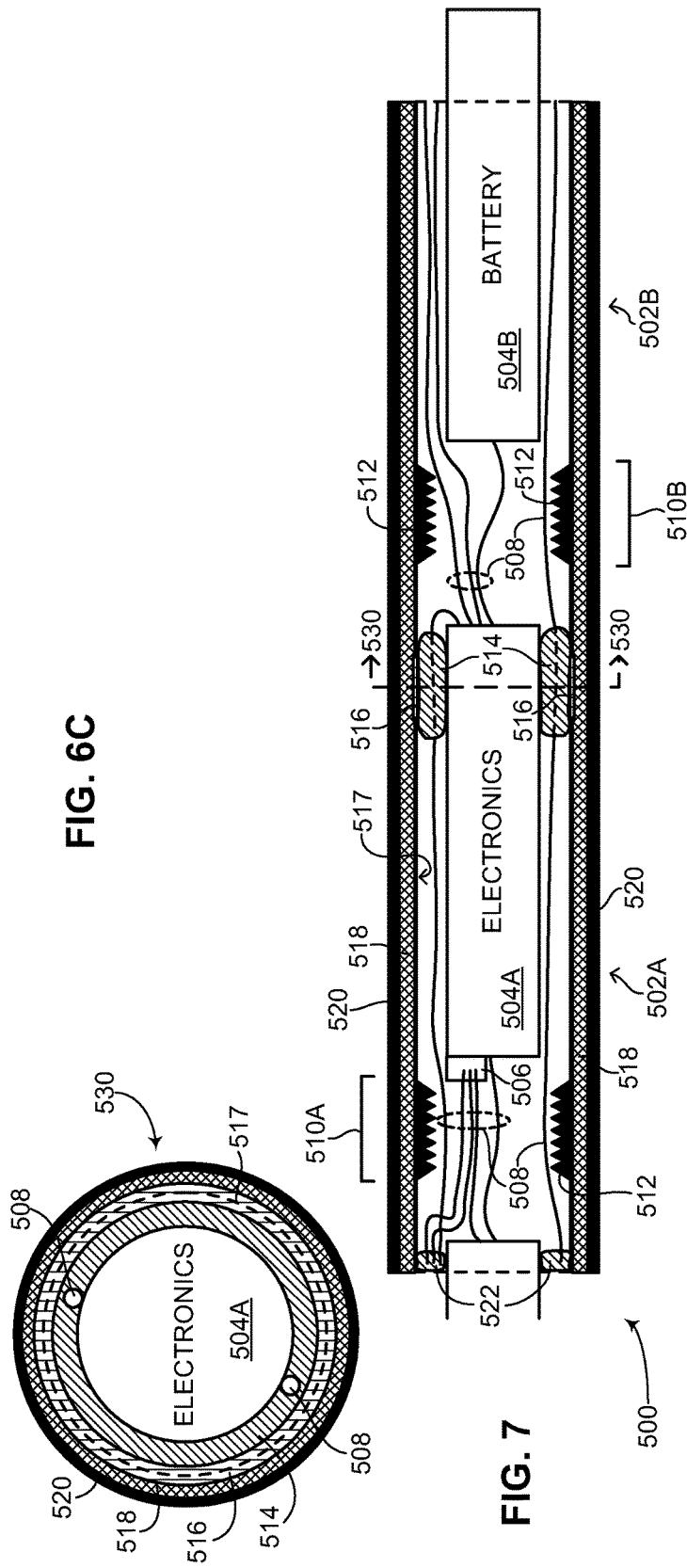

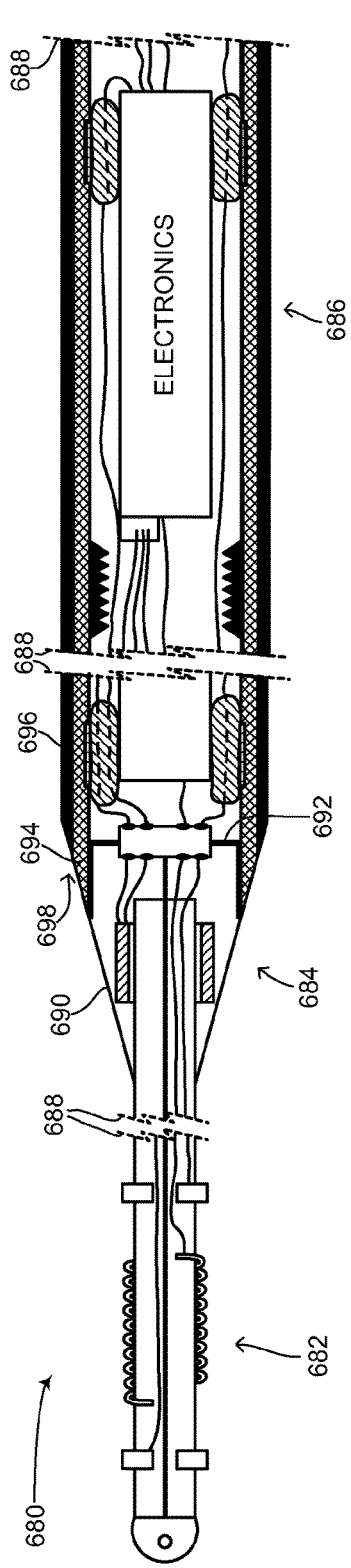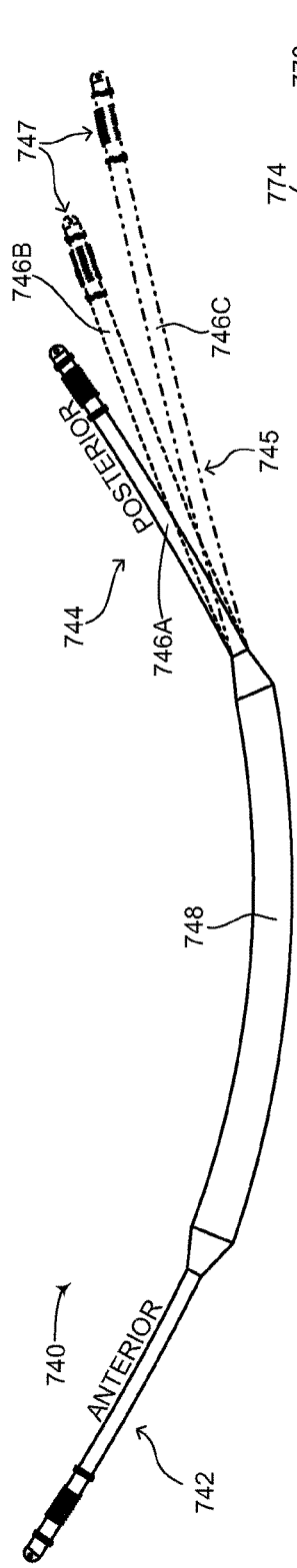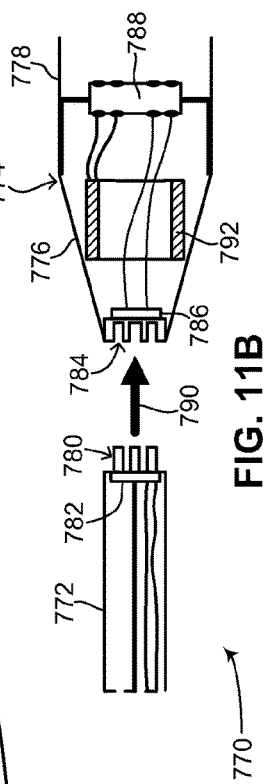

FLEXIBLE RECHARGEABLE IMPLANTABLE SUBCUTANEOUS MEDICAL DEVICE STRUCTURE AND METHOD OF ASSEMBLY

FIELD OF THE DISCLOSED TECHNIQUE

The disclosed technique relates to implantable medical devices, in general, and to subcutaneous pacemakers and implantable cardioverter defibrillators and their methods of assembly, in particular.

BACKGROUND OF THE DISCLOSED TECHNIQUE

An arrhythmia is a medical condition in which there exists a problem with the rate or rhythm of the heartbeat usually due to abnormal electrical activity in the heart. More specific types of arrhythmia include when the heart beats too fast (known as tachycardia), too slow (known as bradycardia) or with an irregular rhythm (known as cardiac fibrillation). Two general devices are known in the art for helping people who experience arrhythmias. One is known as a pacemaker, the other is known as an implantable cardioverter defibrillator (herein abbreviated ICD). Pacemakers are implantable devices which continuously measure the heartbeat and electrical activity in the heart. Pacemakers can detect irregularities in the heartbeat, i.e. arrhythmias, and are programmed to provide electrical signals to the heart to restore its normal beating rhythm.

Reference is now made to FIG. 1A, which is a schematic illustration of a pacemaker or ICD with intravascular leads implanted in a patient, generally referenced 10, as is known in the art. As shown in FIG. 1A, a pacemaker 12 is implanted in a patient 14, having a heart 16 and a ribcage 18. Pacemaker 12 includes two main components, a can 20 and electrical leads 22. Can 20 includes a power source (not shown), such as a battery, as well as an electronic circuit (not shown) for monitoring the electrical activity in the heart and for providing electrical signals to the heart when aberrant rhythms of the heart are detected. The electronic circuit may include at least one low voltage capacitor (not shown). Can 20 is usually implanted in patient 14 via a surgical procedure on his left side adjacent to and below the clavicle bone (also known as the collarbone), as shown by an arrow 24 in FIG. 1A. Electrical leads 22 are coupled with the electronic circuit in can 20 at one end and are coupled intravascularly with heart 16 at the other end, the electrical leads being inserted through the subclavian vein (not shown) and the vena cava (not shown). Electrical leads 22 are typically implanted in patient 14 by inserting them percutaneously through his vena cava (not shown). Once attached to heart 16, they are coupled with can 20. Electrical leads 22 are usually flexible and provide electrical signals of heart 16 to the electronic circuit in can 20 as well as providing electrical signals from the electronic circuit to heart 16. Typically, electrical leads 22 are implanted in right ventricle 26 and right atrium 28 of heart 16.

ICDs are similar to pacemakers and include similar components, such as a can and electrical leads; thus pacemaker 12 in FIG. 1A could also be an ICD. An ICD differs slightly from a pacemaker in that its can includes a power source, electronics, electrical leads as well as at least one high voltage capacitor. The electronics of an ICD includes a sensing algorithm to detect ventricular fibrillation, a functionality not included in standard pacemakers. The difference between an ICD and a pacemaker is that an ICD can deliver a high voltage electric shock to the heart to terminate an otherwise potentially fatal cardiac tachyarrhythmia. A pacemaker is generally limited to treating bradyarrhythmias which can be treated with a significantly lower voltage electric impulse. The presence of at least one high voltage capacitor in an ICD accounts for its difference in function from a pacemaker as the at least one high voltage capacitor enables a significantly higher electrical shock to be built up and delivered to the heart. An additional function of an ICD is to send the heart an electrical shock in case of ventricular fibrillation (herein abbreviated VF) and in order to prevent cardiac arrest, i.e., aborted sudden death. The electrical energy required for the electrical shock is built up and stored in the at least one high voltage capacitor. ICDs exist as standalone devices yet are also manufactured having the functionality of a pacemaker. In addition, cardiac resynchronization therapy defibrillators (herein abbreviated as CRT-D), which are a type of ICD, include a third electrode allowing for simultaneous pacing of both the right and left ventricles of the heart.

As mentioned above, ICDs, similar to pacemakers, constantly monitor the rate and rhythm of the heart and deliver therapies to the heart by way of an electrical shock. In the case of an ICD, electrical shocks are provided to the heart when the measured electrical activity of the heart exceeds a preset number. State of the art ICDs can distinguish different types of aberrant electrical activity in the heart, such as VF, when the heart contracts irregularly, versus ventricular tachycardia (herein abbreviated VT), when the heart beats regularly but significantly faster than normal. In the case of VT, such ICDs may send electrical signals to the heart to try and pace the heart faster than its intrinsic heart rate in an attempt to stop the tachycardia before it progresses to VF. This technique is known in the art as fast-pacing, overdrive pacing or anti-tachycardia pacing (herein abbreviated ATP). As is known to workers skilled in the art, ATP is only effective if the underlying rhythm of the heart is ventricular tachycardia. ATP is never effective if the heart is already experiencing ventricular fibrillation and thus lacks a consistent heart rate. State of the art ICDs use a combination of various methods to determine if received electrical signals from the electrical leads represent a normal rhythm of the heart, ventricular tachycardia or ventricular fibrillation. It is noted that the placement of an ICD in the body of a patient is similar to that of a pacemaker, however in the case of a CRT-D device, the electrical leads can also be implanted in the left side of the heart via the coronary sinus (not shown) of the heart. This is shown in FIG. 1A as an electrical lead 30, denoted by a dashed line. Pacemakers and ICDs with intravascular leads are known in the art. As an example, U.S. Pat. No. 5,133,353 to Hauser, assigned to Cardiac Pacemakers, Inc., entitled "Implantable intravenous cardiac stimulation system with pulse generator housing serving as optional additional electrode" is directed to an implantable cardiac stimulation lead system having pacemaking, cardioversion and higher energy defibrillation capabilities. The implantable cardiac stimulation lead system also has a selectable electrode configuration and utilizes a relatively small number of implantable parts. The lead system comprises a transvenous myocardial, or pericardial lead having a plurality of electrodes as well as pulse generator circuitry. The lead electrodes are capable of sensing and performing standard anti-bradycardia pacing, anti-tachycardia pacing, cardioversion and defibrillation. The transvenous lead is connected to a pulse generator having full-function pacing capabilities as well as cardioversion and defibrillation capabilities. The housing of the pulse generator is conductive and is connected to the pulse generator circuitry so that it may selectively serve as a discharge electrode. The outer surface of the pulse generator could be of a special configuration to facilitate its discharge capabilities. The pulse generator is implanted in the pectoral or abdominal region of the body proximate the heart. A programmable switch or other type of circuitry is provided to select the electrode configuration which may include or exclude the pulse generator housing electrode. As a result, different electrode configurations can be obtained for specific types of cardiac stimulations. Other examples of such heart devices with intravascular leads include U.S. Pat. No. 5,261,400 and WO 2003/002198 (both to Medtronic, Inc.), WO 2004/028628 (St. Jude Medical), U.S. Pat. No. 6,256,541 (Cardiac Pacemakers, Inc.), US 2012/0165913 A1 and EP 1 631 350 B1 (proprietor Cameron Health Inc.).

Known in the art as well are intravascular ICDs, also known as percutaneous ICDs, in which the entire device, including all the components found in a can and the leads, is positioned within the vasculature of a patient. As an example, U.S. Pat. No. 7,899,554 B2 to Williams et al., assigned to Synecor LLC, entitled "Intravascular system and method" is directed to an intravascular implantable pacing and/or defibrillation system. The system includes a pulse generator that is implantable within a blood vessel and at least one electrode attachable to the pulse generator. The pulse generator is proportioned to blood flow through the blood vessel. During implantation, the pulse generator is introduced into a patient's vasculature, advanced to a desired vessel and anchored in place within the vessel. The electrode or electrodes are placed within the heart or surrounding vessels as needed to deliver electrical pulses to the appropriate location. Other examples of such intravascular ICDs are described in U.S. Pat. No. 7,617,007 B2 and U.S. Pat. No. 8,311,633 B2 (all assigned to Synecor LLC). These intravascular ICDs however are not yet available in the market.

Pacemakers and ICDs with intravascular leads, as shown in FIG. 1A, are advantageous in that the electrical leads used for sensing arrhythmias as well as delivering electrical shocks and impulses to the heart are placed directly in the heart (i.e., hence intravascularly). Such a placement of the electrical leads allows for a significantly high signal-to-noise ratio (herein abbreviated SNR) such that aberrant electrical activity detected in the heart is in fact aberrant electrical activity of the heart and not electrical activity coming from another source of electrical activity in the body near the heart or from a source outside the body generating an electric field. Also, the closeness of the electrical leads to the chambers of the heart enables a generally lower voltage to be applied to the heart for either pacing it or for treating VT or VF via electrical shocks. Such pacemakers and ICDs however are disadvantageous in that major surgery is required to implant the can in the body and the electrical leads in the vasculature of the heart. This disadvantage is true of intravascular ICDs as well as the entire device must be implanted in the vasculature of the patient. Furthermore, when the energy of the battery is depleted, or if there is a problem with the electrical leads placed in the heart, the patient must undergo further surgery to either replace the entire can or to have new electrical leads placed in the heart. Pacemakers and ICDs having cans with replaceable and/or rechargeable batteries are currently not on the market, thus when the battery of such devices is depleted, the entire can of the device (pacemaker or ICD) must be replaced.

In the past decade, there has been a general trend in surgery and implantable medical devices to reduce the amount of invasiveness of either the surgery involved or the positioning of the implantable medical device in the body of a patient. For example, in the field of ICDs, medical device companies have begun researching and developing subcutaneous ICDs which are to be placed under the skin and around the heart, thereby significantly reducing the invasiveness of an implanting procedure and the actual positioning of the ICD in the body of the patient. One of the reasons for this trend in ICDs is that many health-related issues have occurred with the intravascular and intracardiac leads used in prior art ICDs, including the recall of such leads. Intravascular and intracardiac leads move a tremendous amount within the heart as it beats during the lifespan of a prior art ICD. With an average of 60 movements per minute over the course of seven years, an intravascular lead may move over 220 million times. These leads thus require a very high durability due to the continuous movement of these leads within the heart and can wear and break over time, causing serious problems to the patient, including patient death. Major companies in this field include Boston Scientific, Cameron Health (acquired by Boston Scientific), Medtronic and St. Jude Medical. Of these companies, only Cameron Health has an actual subcutaneous ICD device in the market.

Reference is now made to FIG. 1B, which is a schematic illustration of a subcutaneous ICD implanted in a patient, generally referenced 40, as is known in the art. A patient 44 is shown, having a heart 46 and a ribcage 48. A subcutaneous ICD 42 in placed under the skin near the heart. Subcutaneous ICD 42 includes a can 50 and electrical leads 52, each respectively similar to can 20 (FIG. 1A) and electrical leads 22 (FIG. 1A). Can 50 can also be referred to as a canister. Can 50 is usually positioned under the skin around a fifth left rib 51, near the heart (i.e., laterally to the heart), whereas electrical leads 52 are positioned around heart 46. Usually a first electrical lead is positioned anterior to heart whereas a second electrical lead is positioned posterior to heart, thus creating an electrical shock vector between the two electrical leads via heart 46. Subcutaneous ICD 42 thus also has a can and leads configuration, similar to pacemaker 10 (FIG. 1A). Subcutaneous ICDs having a can and leads configuration are known in the art. As an example, U.S. Pat. No. 6,721,597 B1 to Bardy et al., assigned to Cameron Health, Inc., entitled "Subcutaneous only implantable cardioverter defibrillator and optional pacer" is directed to a subcutaneous implantable cardioverter-defibrillator (S-ICD) having an electrically active canister which houses a battery supply, capacitor and operational circuitry where the canister serves as an electrode and replaces one conventional lead of a traditional system. The canister also has one or more subcutaneous combined high voltage/sense/pace electrodes and sense circuitry suitable to an ICD or AED V-FIB detection algorithm. The S-ICD further has an application system for simple insertion of the subcutaneous lead and a cutaneous test system designed to estimate the best location of the S-ICD for each patient. Cardioversion-defibrillation energy is delivered when the operational circuitry senses a potentially fatal heart rhythm. There are no transvenous, intracardiac or epicardial electrodes used in the S-ICD. Other examples include the following patents and patent applications: U.S. Pat. No. 8,483,841 B2, U.S. Pat. No. 8,644,926 B2 (all assigned to Cameron Health Inc.), U.S. Pat. No. 8,260,415 B2, U.S. Pat. No. 8,512,254 B2, U.S. Pat. No. 8,359,094 B2, U.S. Pat. No. 7,894,894 B2 (all assigned to Medtronic Inc.) and EP 2 510 973 A1 (applicant Cardiac Pacemakers Inc.).

Subcutaneous ICD 42 is advantageous over an ICD with intravascular leads and an intravascular ICD in that major surgery is not involved in its placement and improved safety is provided to the patient since the insertion of the electrical leads of the ICD does not involve any intervention with the heart or puncturing of a blood vessel. Replacing can 50 or replacing electrical leads 52 if they are faulty is also simpler in that only percutaneous surgery is involved. However, since subcutaneous ICD 42 and its electrical leads are not placed in the vasculature of the heart, electrical leads 52 may have a significantly lower SNR and thus the electric circuit (not shown) in can 50 may have a harder time differentiating between electrical activity of the heart and what is known in the field as extra-cardiac oversensing or extra-cardiac noise (i.e., electrical activity sensed from non-cardiac muscles around the heart and electrical activity coming from sources outside the patient). This difficulty in differentiating between true electrical activity of the heart and extra-cardiac oversensing can lead to subcutaneous ICD 42 delivering shocks to the heart when it doesn't need it and also failing to deliver shocks to the heart when it does need it. In addition, since electrical leads 52 are not placed directly in heart 46, a higher voltage must be applied to the leads for treating VT or VF via electrical shocks as compared with conventional ICDs (as in FIG. 1A) in which its leads are placed intravascularly directly in the heart. The higher voltage requires a higher level of energy. The higher level of energy thus requires a larger can volume since the can requires a larger battery and larger high voltage capacitors to provide the higher energy requirements. The can and leads configuration of subcutaneous ICD 42 may also cause discomfort to patient 44, especially considering that the rigid outer surface of can 50 is placed directly on ribcage 50 where humans in general do not have a lot of excess skin or fat tissue in this particular region of the body to cushion can 50. A further disadvantage of a subcutaneous ICD is that due to its placement in a patient, many sensory and motor nerves are located between the electrical leads. Any stimulation generated between the electrical leads for the heart will be felt by the patient as both muscle contractions (i.e., from the motor nerves) and pain (i.e., from the sensory nerves). This is much less of a concern for an ICD with intracardiac leads, especially when stimulation is generated between the leads in the heart, as the electric field generated is essentially limited to the area of the heart and does not cause muscle contractions or the sensation of pain around the heart. If it for this reason that subcutaneous ICDs generally do not provide a pacing function.

Some of the concerns with subcutaneous ICD 42 have been mitigated by medical device companies using a different configuration for subcutaneous ICDs, such as a curved configuration. Reference is now made to FIG. 1C, which is a schematic illustration of another subcutaneous ICD implanted in a patient, generally referenced 70, as is known in the art. A patient 74 is shown having a heart 76 and a ribcage 78. A subcutaneous ICD 72 in placed under the skin near the heart. Subcutaneous ICD 72 includes a housing 73. Housing 73 includes a plurality of surface electrodes 80, an electric circuit (not shown), a battery (not shown) and at least one high voltage capacitor (not shown), similar to the elements found in subcutaneous ICD 42 (FIG. 1B). Housing 73 has a curved configuration, being thin, narrow and flexible, similar to a patch, bandage or plaster and shaped to fit around a patient's rib. Plurality of surface electrodes 80 are positioned on one side of housing 73, giving subcutaneous ICD 72 a specific directionality. As shown in FIG. 1C, a first surface electrode 82A and a second surface electrode 82B are placed on an inner side of housing 73, facing towards the body (not labeled) of patient 74. As compared with subcutaneous ICD 42, subcutaneous ICD 72 does not have any electrical leads. Instead first surface electrode 82A and second surface electrode 82B are used to both sense electrical activity of heart 76 as well as apply electrical shocks to heart 76. Plurality of surface electrodes 80 thus function as electrical leads.

Housing 73 is usually positioned under the skin around a fifth left rib 84, near the heart. Since housing 73 is flexible, it is usually wrapped around fifth left rib 84, or near it, following the contours of ribcage 78 and partially wrapping around heart 76. A proximal end (not labeled) of housing 73 may be anterior to heart 76 and a distal end (not labeled) of housing 73 may be posterior to heart 76. An electrical shock vector is thus created between plurality of surface electrodes 80 via heart 76. It is noted that housing 73 is usually made of metal and can also function as a sensor or electrical lead. Housing 73 is thus also referred to in the art as an active can. In such a configuration, one of the surface electrodes can be used to sense electrical activity whereas the other surface electrode can be used with housing 73 to create an electrical shock vector. Subcutaneous ICDs having a curved configuration are known in the art. As an example, U.S. Pat. No. 6,647,292 B1 to Bardy et al., assigned to Cameron Health, entitled "Unitary subcutaneous only implantable cardioverter-defibrillator and optional pacer" is directed to a unitary subcutaneous implantable cardioverter-defibrillator having a long thin housing in the shape of a patient's rib. The housing contains a source of electrical energy, a capacitor and operational circuitry that senses the presence of potentially fatal heart rhythms. Provided on the housing are cardioversion/defibrillation electrodes located to deliver electrical cardioversion-defibrillation energy when the operational circuitry senses a potentially fatal heart rhythm. The unitary subcutaneous implantable cardioverter-defibrillator does not have a transvenous, intracardiac, epicardial or subcutaneous electrode. Other examples include the following patents: U.S. Pat. No. 7,363,083 B2, U.S. Pat. No. 8,718,760 B2 (all assigned to Cameron Health Inc.) and U.S. Pat. No. 7,684,864 B2 (assigned to Medtronic Inc.).

Whereas subcutaneous ICD 72 may be more comfortable for a patient than subcutaneous pacemaker 42 (FIG. 1B) due to its flexible thin shape and slightly reduced invasiveness since only a single element needs to be implanted in patient 74, surgery is still required to replace a dead battery in subcutaneous ICD 72. In addition, subcutaneous ICD 72 may suffer the same SNR issues that accompany subcutaneous ICD 42 in terms of differentiating true cardiac electrical activity compared to extra-cardiac oversensing. In addition, as mentioned above subcutaneous ICD 72 has a particular directionality and must be placed in a specific orientation to function properly in patient 74.

SUMMARY OF THE DISCLOSED TECHNIQUE

The disclosed technique provides for a novel flexible implantable subcutaneous heart device (HD) structure and a novel method for positioning a flexible implantable subcutaneous HD in a patient, which overcome the disadvantages of the prior art. According to one embodiment of the disclosed technique there is thus provided a flexible implantable subcutaneous HD structure which includes a flexible device body, at least one flexible lead and at least one respective transition unit. The respective transition unit is for respectively coupling each flexible lead to the flexible device body. The flexible device body includes a plurality of inner components and a respective plurality of hollow outer units. The hollow outer units are for encasing and protecting the inner components. Each one of the hollow outer units includes at least one hollow rigid element and a hollow flexible element. The hollow flexible unit is coupled with the hollow rigid element for enabling the outer unit a degree of flexibility. The hollow flexible element is covered with a covering and the flexible device body is covered with a polymer.

According to another embodiment of the disclosed technique there is thus provided a method for positioning a flexible implantable subcutaneous heart device (HD), wherein the flexible implantable subcutaneous HD includes a flexible device body, an anterior flexible lead and a posterior flexible lead. The method includes the procedures of positioning the anterior lead substantially near a sternum of a patient, positioning the posterior lead substantially in a back of the patient and positioning the flexible device body below a ribcage of the patient.

BRIEF DESCRIPTION OF THE DRAWINGS

The disclosed technique will be understood and appreciated more fully from the following detailed description taken in conjunction with the drawings in which:

FIG. 6C is a schematic illustration showing an embodiment for covering the flexible section of a third outer unit design, constructed and operative in accordance with another embodiment of the disclosed technique;

FIG. 7 is a schematic illustration showing the interior and cross-section of the flexible device body of the medical device structure of FIG. 2, constructed and operative in accordance with a further embodiment of the disclosed technique;

FIG. 10 is a schematic illustration showing the interior of the medical device structure of FIG. 2, constructed and operative in accordance with a further embodiment of the disclosed technique;

FIG. 11A is a schematic illustration of the medical device structure of FIG. 2 showing various lengths for the posterior lead, constructed and operative in accordance with another embodiment of the disclosed technique;

FIG. 11B is a schematic illustration of the interior of an end coupler, strain relief and lead of the medical device structure of FIG. 2 in which the lead is detachable, constructed and operative in accordance with a further embodiment of the disclosed technique;

DETAILED DESCRIPTION OF THE EMBODIMENTS

Figure 1A:
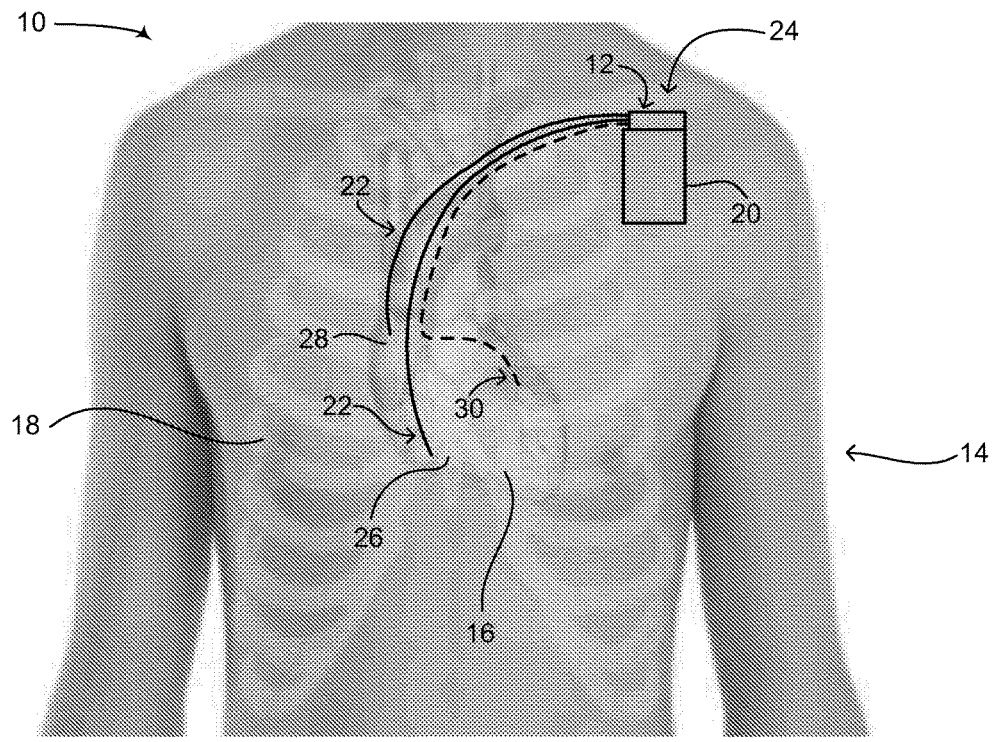
FIG. 1A is a schematic illustration of a pacemaker or ICD with intravascular leads implanted in a patient, as is known in the art.

The disclosed technique overcomes the disadvantages of the prior art by providing a novel flexible rechargeable implantable subcutaneous medical device, structure and method of assembly. The flexible device structure of the disclosed technique can be used to construct and fabricate a variety of implantable medical devices (herein abbreviated IMDs) which are implantable subcutaneously. Examples of such devices include: pacemakers, CRT-Ds, ICDs, cardiac rhythm monitors, neurostimulators, electrically stimulating pain control devices, drug delivery devices as well as numerous implantable sensing devices. According to the disclosed technique, the IMDs may be embodied as wirelessly rechargeable devices or non-rechargeable devices. Implantable sensing devices can include devices used to sense physiological parameters such as transthoracic impedance, subcutaneous oxygen, pH levels, glucose levels, respiratory rate, electrical activity of the heart or other muscle groups, position of a patient, acceleration of the patient and body temperature. The disclosed technique integrates the main elements of an IMD, such as a power source, electronics and possibly at least one capacitor (either low voltage, high voltage or both) in a flexible symmetric narrow device body which can be implanted subcutaneously in the body. The flexible nature of the device body allows the IMD of the disclosed technique to be comfortably and easily placed subcutaneously in the body without impeding patient movement yet also minimizing patient discomfort. The symmetric nature of the device body eliminates any directionality or particular orientation of the IMD of the disclosed technique such that once the device body is implanted, even if it moves or rolls, functionality of the IMD is not compromised and the IMD remains fully functional. The IMD of the disclosed technique is minimally invasive, requiring either one, two or three small incisions for subcutaneous implantation and obviates the need for repeated surgeries to replace dead batteries as the IMD of the disclosed technique is wirelessly rechargeable using energy transfer methods and inductive charging and can be recharged while the IMD remains inside the body of a patient. As mentioned above, prior art subcutaneous IMDs such as subcutaneous ICDs may need a higher voltage as compared with intravascular pacemakers and ICDs to function effectively as they are further from the heart. This results in an increase in the size and number of batteries required in prior art subcutaneous ICDs. According to the disclosed technique, the size and number of batteries for a subcutaneous IMD can be significantly reduced since the IMD of the disclosed technique can be recharged wirelessly. The IMD of the disclosed technique can store less electric energy to be used in monitoring a patient and providing electric shocks and impulses to the patient since the batteries used to build up the electric charge can be recharged. In prior art subcutaneous ICDs, the electric energy necessary for the life of the IMD needs to be present in the device since the batteries cannot be recharged, thereby resulting in the need for more batteries (i.e., more stored energy) which in total are larger in size. This concern is mitigated by the IMD of the disclosed technique. The rechargeable aspect of the IMD of the disclosed technique enables the IMD of the disclosed technique to function and operate significantly longer, for example between 7-10 years and in some cases even 15 years (as was shown scientifically in other lithium-ion rechargeable devices), as compared to prior art IMDs, which may last between 5-7 years before the battery and thus the whole device needs replacement.

In one embodiment of the disclosed technique, the IMD is a unitary device and includes two leads which enable signals in the body of a patient to be detected and electrical impulses or shocks to be delivered to a target location in the patient. In this embodiment, the two leads form part of the unitary device, making the IMD of the disclosed technique a single unit. In another embodiment of the disclosed technique, the two leads may be detachable, thus enabling a single device body to be coupled with various types of leads, both in terms of function, length and size. Unlike the prior art, the IMD of the disclosed technique does not include an active can which can also function as a lead. Thus at minimum, two leads are required. It is noted that the IMD of the disclosed technique, depending on its use in the body, can be constructed to have more than two leads while still maintaining a unitary shape. For example, in one embodiment of the disclosed technique, a unitary device body, comprised of segments, coupled with two leads may have at least one segment or portion of the unitary device body be electrically active, thus enabling more than one possible electric shock vector between the two leads. In this embodiment, the unitary device body is not an active can as the entire unitary device body is not electrically active; only a portion or segment, or a number of portions or segments are electrically active. The active segment or segments are also not active cans since they are open on both ends, as described below. In a further embodiment of the disclosed technique, the IMD can include at least one lead provided it is long enough to accommodate two electrical impulse delivery electrodes (i.e., shocking coils) spaced far enough apart to create a shock vector. In general, such an embodiment is possible provided the location of the at least one lead and its length are sufficient to generate a sufficient energy density over the heart to cause cardioversion. In an IMD placed subcutaneously around the heart, cardioversion is possible provided about 80% of the left ventricle of the heart is shocked with at least 3.5 joules per centimeter of energy.

The IMD of the disclosed technique is easily implanted and easily removed from the patient and is cost effective to manufacture and assemble. The cost effectiveness of the disclosed technique is due to a number of factors. First, the IMD of the disclosed technique is relatively simple in functionality as explained below, thus making it cost effective. Second, since the IMD integrates all its elements into a single component, various packaging and manufacturing costs can be reduced as compared to a system which includes multiple components that need to be manufactured and packaged separately. Not having a connector between the lead or leads and the device body also reduces the possible number of points of failure in the IMD of the disclosed technique as well as reducing the possibility of leakage of body fluids into the device. Furthermore, the lack of a connector between the lead or leads and the device body also increases reliability, since in the case of a connector in an IMD, a connection needs to be made between those parts by the physician when the IMD is implanted (thus leaving open the possibility of an improper connection made during implant surgery), whereas in the case of the disclosed technique where the IMD is a unitary device, the device is tested by a technician in laboratory settings before being sent to a physician for use in a patient (thus less chance of device failure or faulty connections in the device before implant surgery).

As described below, the device structure of the subcutaneous IMD of the disclosed technique is substantially different than the device structure of intravascular IMDs. Intravascular IMDs require a delivery catheter or a delivery procedure to insert the IMD into the blood vessels of a patient. In addition, the IMD remains in the blood vessels of the patient. The IMD of the disclosed technique is implanted subcutaneously and therefore does not require a delivery catheter since the IMD is pulled or pushed under the skin of the patient. The IMD of the disclosed technique also does not require a blood vessel to be opened or for any part to remain in a blood vessel of the patient. The IMD of the disclosed technique does however require an insertion tool which paves the way for the IMD and a wire to be used to pull the IMD through the skin. Such an insertion tool however is different than a delivery catheter as it is not inserted into the vasculature of a patient but remains in the subcutaneous space. Intravascular IMDs require a stent-like structure or a fixation structure, such as a screw, to hold them in place inside the vasculature of the patient where blood flows or to hold leads in place inside the heart, resulting in risks to the patient, including puncturing of the heart and/or major blood vessels. The IMD of the disclosed technique is implanted subcutaneously and does not require a stent-like structure to maintain its position once implanted in the patient, for example as compared with the intravascular ICD disclosed in U.S. Pat. No. 7,899,554 B2. Alternatively, an embodiment of the IMD of the disclosed technique may use a suture or suture sleeve to maintain its position once implanted in a patient, The IMD of the disclosed technique also does not require any such fixation structures aside from suture sleeves and/or eyelets for affixing the IMD to subcutaneous tissue. As described below, one, two or three suture eyelets or insertion holes are provided in the IMD for simply and easily affixing the IMD to the body of the patient and for limiting the movement of the IMD inside the patient once implanted. Intravascular IMDs usually have multiple electrodes positioned along the entire length of the IMD, and generate a shock vector through an organ, such as the heart, based on the position and curvature of the vasculature of the patient. In one embodiment of the disclosed technique, the IMD of the disclosed technique includes only two electrical impulse delivery electrodes which are positioned at opposite ends of the IMD. Other embodiments are possible as described above, such as the case of an IMD having at least one active segment in addition to the leads. The possible directions of the shock vector generated through an organ according to the IMD of the disclosed technique are substantially more versatile as the subcutaneous space in a patient has a greater degree of freedom than the vasculature, since the vasculature defines specific paths and locations in the body whereas the subcutaneous space substantially spreads continuously over the entire body. For example, in the case of an ICD, the IMD of the disclosed technique can deliver a shock vector which passes through the heart from the chest to the back (or vice-versa) of the patient.

Intravascular IMDs or percutaneous IMDs, especially in the case of intravascular ICDs, require less energy to deliver an effective shock to the heart of a patient due to their proximity to the heart. An intravascular ICD, for example, has less design constraints in terms of space usage since less energy and capacitors are required to generate an effective shock to the heart. In the case of the IMD of the disclosed technique being embodied as a subcutaneous ICD, the location of the subcutaneous ICD is further from the heart than in the case of an intravascular ICD. A subcutaneous ICD therefore requires more energy to deliver an effective shock to the heart of the patient. This increase in energy requirement also increases the design constraints of a subcutaneous ICD, since more stored energy (which usually implies more batteries) and capacitors may be needed to achieve the required energy levels for effective electrical shocks however there is still the desire to have a device which is as small as possible. As described below, the IMD structure of the disclosed technique, in the case of a subcutaneous ICD, enables sufficient batteries and capacitors to deliver an effective subcutaneous electrical shock to the heart to be included in the IMD structure while also minimizing the volume required to encase all those elements.

Other differences between an intravascular IMD and a subcutaneous IMD, such as the subcutaneous IMD of the disclosed technique, include the following:

subcutaneous IMDs sense parameters (for example, electrical activity in the heart) from different tissue layers and different locations in the body of a patient than intravascular IMDs;

subcutaneous IMDs experience different pulling and tensile forces due to their placement in the subcutaneous space of a patient than the pulling and tensile forces of an IMD placed in the vasculature of the patient;

design limitations such as length and width are based on the location of where an IMD is placed in the body. Therefore, in the case of an intravascular IMD, such limitations are based on the dimensions of blood vessels whereas in the case of a subcutaneous IMD, such limitations are based on dimensions of body circumference, available subcutaneous space, and the like. For example, intravascular IMDs may be more limited in length and thickness due to their placement in the vasculature, whereas subcutaneous IMDs according to the disclosed technique might be less limited in terms of length and thickness. For example, intravascular IMDs need to meet limitations such as a thickness of no more than 1 centimeter and a length not exceeding 50-55 centimeters, whereas subcutaneous ICDs of the disclosed technique might be as thick as 1.3 centimeters (if not even thicker) and as along as 70-80 centimeters. In addition, individual components of a subcutaneous IMD might need to be shorter in length in order to enable increased flexibility in the subcutaneous space;

subcutaneous IMDs can be easier to recharge wirelessly than intravascular IMDs, as they are positioned closer to the outside surface of the skin of a patient where a recharging element may be placed; and different bodily fluids are located in and surround the subcutaneous space as compared with the vasculature. For example, the vasculature is directly exposed to blood whereas the subcutaneous space is not.

In general, the disclosed technique is described herein using an ICD as an example, however as mentioned above, the disclosed technique can be applied to any subcutaneous IMD, such as a subcutaneous CRT-D or a subcutaneous pacemaker. Thus, as an example a flexible rechargeable implantable subcutaneous ICD is described below in terms of its structure and functionality, including a method of assembly. The structure disclosed includes the mechanical structure as well as the electrical structure of a subcutaneous IMD. The subcutaneous ICD of the disclosed technique includes the following characteristics:

can provide any known stimulation type therapy to the heart, wherein the heart, or a part thereof, is stimulated via electrical impulses or electrical shocks;

is embodied as a single unit, including a power source (such as a battery), leads and any other electronics (such as a CPU, at least one high voltage capacitor and the like) required to provide the electrical impulses or electrical shocks as stimulation (thus not having a separate can and leads configuration as described in the prior art);

can be positioned inside a patient subcutaneously;

has a generally tubular or cylindrical shape with a cross-sectional shape having any known curvature. For example, the cross-sectional shape may be a circle, an ellipse or a closed curve. The cross-sectional shape may also be any conic section having an eccentricity ranging from 0 to 1. The cross-sectional shape is substantially symmetrical.

Figure 2:
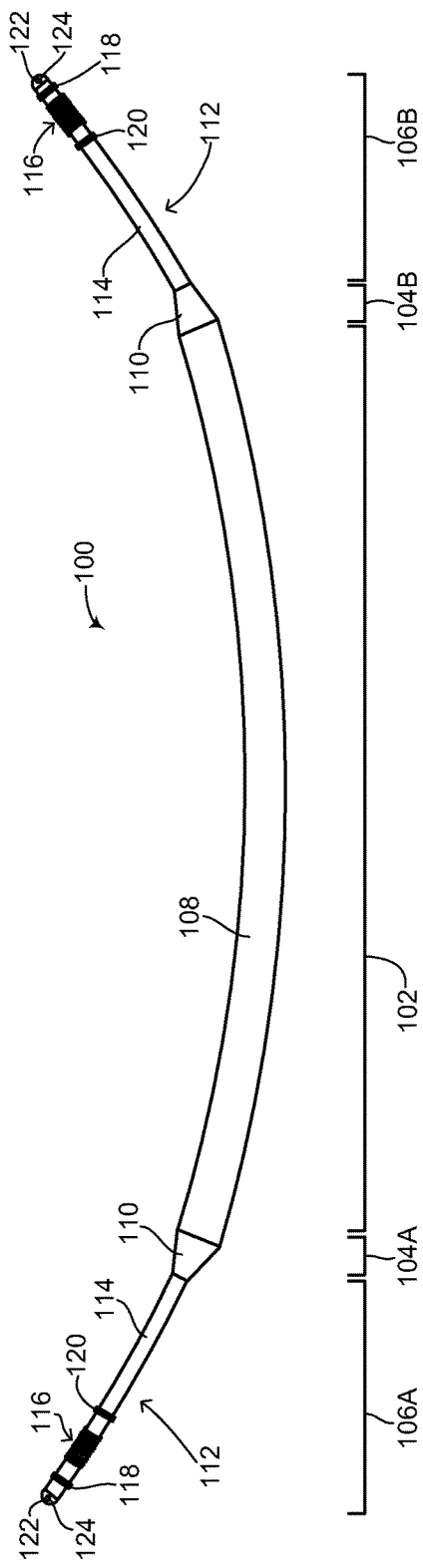
FIG. 2 is a schematic illustration of a flexible rechargeable implantable subcutaneous medical device structure, constructed and operative in accordance with an embodiment of the disclosed technique.

The subcutaneous ICD of the disclosed technique relates in particular to the structural configuration of a subcutaneous ICD as well as its method of assembly. Reference is now made to FIG. 2, which is a schematic illustration of a flexible rechargeable implantable subcutaneous medical device structure, generally referenced 100, constructed and operative in accordance with an embodiment of the disclosed technique. As mentioned above, subcutaneous medical device structure 100 is shown embodied as a subcutaneous ICD. FIG. 2 shows the outside of subcutaneous ICD 100 and the main components and elements which comprise its structure. Subcutaneous ICD 100 includes a flexible device body 108, a plurality of flexible leads 112 and a respective plurality of transition units 110. Flexible device body 108 is hermetically sealed. Each flexible lead 112 is coupled to flexible device body 108 via a respective transition unit 110. The various sections of subcutaneous ICD 100 are shown by a plurality of divider lines. A divider line 102 delineates flexible device body 108, a divider line 104A delineates an anterior transition unit 110, a divider line 104B delineates a posterior transition unit 110, a divider line 106A delineates a flexible anterior lead 112 and a divider line 106B delineates a flexible posterior lead 112. It is noted that since the disclosed technique applies to a subcutaneous IMD and not just a subcutaneous ICD, the structure of the subcutaneous IMD includes a device body and at least one lead. In another embodiment of the disclosed technique, the structure of the subcutaneous IMD includes a device body, at least one lead and at least one active segment, as described below in FIGS. 13A-13C. Whereas an ICD (as shown in FIG. 2) and a pacemaker both require two leads to function properly, other types of IMDs may not require two leads for proper functioning and thus according to the disclosed technique, such other types of IMDs may structurally have a device body and a single lead coupled to it via a single transition unit. In some embodiments, the device body may have at least one active segment or portion. In addition, according to the disclosed technique, IMDs can be constructed which might not require any leads at all, such as pain control devices and drug delivery devices. Such devices are also contemplated as part of the disclosed technique and can be constructed as described below as a flexible device body without any leads or transition units. It is further noted that subcutaneous ICD 100 can be embodied as a wirelessly rechargeable device or as a non-rechargeable device.

Flexible device body 108 includes two main sections (both not shown), an inner components section and an outer units section. The inner components section is described in greater detail in FIG. 3. The outer units section is described in greater detail in FIG. 4A-6C. Flexible device body 108, including both main sections is described in greater detail in FIG. 7. Each of plurality of transition units 110 includes a respective end coupler and strain relief (both not shown). The structure of the end coupler and strain relief is described in greater detail in FIGS. 8A-8B. Each one of plurality of flexible leads 112 includes a tubular section 114, an electrical impulse delivery electrode 116, a first sensing ring 118, a second sensing ring 120, a tip section 122 and a suture eyelet 124. It is noted that second sensing ring 120 is optional. In general, each one of plurality of flexible leads 112 includes at least one sensing ring. The structure of each of plurality of flexible leads 112 is described in greater detail in FIG. 9.

Both flexible device body 108 and plurality of flexible leads 112 generally have a tubular shape, with flexible device body 108 having a first diameter (not shown) and plurality of flexible leads 112 having a second diameter (not shown). Flexible device body 108 and plurality of flexible leads 112 are both flexible structures, however plurality of flexible leads 112 may have greater flexibility than flexible device body 108. In general, the first diameter is substantially uniform along the length of flexible device body 108 whereas the second diameter is substantially uniform along the length of plurality of flexible leads 112, thus giving subcutaneous ICD 100 two isodiametric sections with a gradually tapering transition between the two sections of the device. This makes subcutaneous ICD 100, in effect, a unitary device with a circular but non-uniform diameter. The first diameter is larger than the second diameter. Plurality of transition units 110 transition between the different diameters of flexible device body 108 and plurality of flexible leads 112. Thus, the overall shape of subcutaneous ICD 100 is cylindrical over its length, albeit with different sections having different diameters. Plurality of transition units also serve to seal flexible device body 108 from any liquids or moisture, while simultaneously enabling wires in plurality of flexible leads 112 to couple with wires in flexible device body 108, and vice-versa.

Flexible device body 108 includes some of the main components required for a functional ICD, such as a power source (not shown), at least one high voltage capacitor (not shown) and electronics (not shown). The power source may be at least one battery (not shown) and is used to power the electronics as well as to build up charge on the at least one high voltage capacitor. The at least one high voltage capacitor is used for delivering electrical shocks and impulses to the heart of a patient (not shown) via electrical impulse delivery electrode 116 of each of plurality of flexible leads 112. The electronics may include a processor, a decision circuit and other related components (all not shown) for receiving electrical signals sensed by at least one of first sensing ring 118 and second sensing ring 120 of each of plurality of flexible leads 112. The electronics analyzes the received electrical signals and determines if the patient is experiencing an arrhythmia and if so, what kind of electrical impulse treatment the patient should receive to terminate the arrhythmia. If a particular treatment is decided upon, the electronics then sends a signal to the at least one high voltage capacitor to discharge its built up charge to electrical impulse delivery electrode 116 of each of plurality of flexible leads 112, thereby providing an electrical impulse to the heart of the patient.

Tubular sections 114 of each of plurality of flexible leads 112 substantially form the main component of plurality of flexible leads 112 and may be more flexible than flexible device body 108. The distal end of tubular section 114 includes tip section 122 which may be rounded, thereby providing a smooth end surface for subcutaneous ICD 100 and preventing its ends from having jagged or rough edges, which is undesirable in a subcutaneous IMD. Tip section 122 may be manufactured as a part of tubular section 114 or may be a separate part glued to the end of tubular section 114. Tip section 122 includes suture eyelet 124, which may be used by a surgeon or physician for attaching each tip section 122 to the body of the patient. For example, once subcutaneous ICD 100 has been implanted in a patient, the surgeon or physician may suture each tip section 122 to skin tissue or muscle tissue using suture eyelet 124, thereby preventing subcutaneous ICD 100 from excessive movement or migration in the body of the patient. It is also possible to use a suture sleeve (not shown) on top of flexible device body 108 to affix flexible device body 108 to skin or muscle tissue. Such a suture sleeve can also be used along plurality of flexible leads 112, if fixation of the lead to subcutaneous tissue is desired not at tip section 122 but somewhere along the lead, for example where the lead needs to be bent to accommodate anatomical constraints of the patient.

Tubular section 114 may be hollow or may include hollow channels for passing and feeding electrical wires and cabling, as described below in FIG. 9. First sensing ring 118 and second sensing ring 120 are metal rings firmly positioned on the outer surface of tubular section 114. Each of first sensing ring 118 and second sensing ring 120 is coupled with a separate wire (not shown) which runs through the hollow or hollow channels of tubular section 114 to transition unit 110. As mentioned above, first sensing ring 118 and second sensing ring 120 are used to detect electrical activity of the heart and to provide such detected activity to electronics (not shown) in flexible device body 108. Electrical impulse delivery electrode 116 is also firmly placed on the outer surface of tubular section 114 and is coupled with a separate wire (not shown) running through the hollow or hollow channels of tubular section 114 to transition unit 110. As shown in FIG. 2, electrical impulse delivery electrode 116 is positioned between first sensing ring 118 and second sensing ring 120. Other arrangements and configurations of electrical impulse delivery electrode 116, first sensing ring 118 and second sensing ring 120 are possible and are a matter of design choice. Electrical impulse delivery electrode 116 is an electrode or coil capable of providing a low voltage or high voltage shock to the heart of the patient. As previously mentioned, the configuration shown in FIG. 2 includes an electrical impulse delivery electrode (as known as a shocking coil) positioned between two sensing rings. This configuration is brought merely as an example and other configurations, including ones that have more shocking coils and more sensing rings are also possible and are a matter of design choice and function for a subcutaneous IMD.

Besides transition from the different diameters of flexible device body 108 and plurality of flexible leads 112, each transition unit 110 enables internal wiring in plurality of flexible leads 112 and internal wiring in flexible device body 108 to be coupled together. As described in detail below in FIGS. 8A and 8B, wires coupling first sensing ring 118 and second sensing ring 120 are coupled with the electronics (not shown) in flexible device body 108 via transition unit 110. Each transition unit 110 may include an electrical feed-through, a filter and the like (all not shown) for enabling electrical wiring in flexible device body 108 and plurality of flexible leads 112 to be coupled in a liquid-proof manner while also being dielectrically shielded and shielded from electrical and magnetic interference.

In general, the approximate ratio in length of flexible device body 108 to plurality of flexible leads 112 may be between 50:50 to 40:60. For example, flexible device body 108 may be 33-34 centimeters (herein abbreviated cm) in length, whereas each one of plurality of flexible leads 112 may be between 15-20 cm in length. As described below in FIG. 11A, a posterior lead (not labeled) of subcutaneous ICD 100 may be longer than an anterior lead (not labeled) of subcutaneous ICD 100 to enable proper placement of the posterior lead in the back of a patient and to accommodate various patient sizes. For example, the anterior lead may measure (but is not limited to) between 15-20 cm in length, whereas the posterior lead may measure (but is not limited to) between 20-30 cm in length. Variations in the length of the posterior lead will allow subcutaneous ICD 100 to accommodate various different patient body sizes without necessitating changes to the other components of the device. This is discussed below as well with reference to FIG. 11A.

It is noted that subcutaneous ICD 100 may include additional components (not shown) for enhancing its functionality. For example, in one embodiment, subcutaneous ICD 100 may include at least one microphone for listening to the heartbeat of the patient. This may assist the decision circuit of the electronics in determining if a sensed electrical signal is a true signal from the heart or merely extra-cardiac oversensing. This may be achieved by data fusion of the sound picked up by the microphone together with electrical signals received from the sensing rings. The at least one microphone may be positioned in flexible device body 108, plurality of transition units 110 or plurality of flexible leads 112. In another embodiment, subcutaneous ICD 100 may also include a pressure sensor (not shown) to sense the contraction of the aorta of the patient and thus determine if blood is flowing in the body. In a further embodiment, subcutaneous ICD 100 may include a Doppler ultrasound sensor (not shown) for sensing blood flow through the major blood vessels of the body. In another embodiment, subcutaneous ICD 100 may include a moisture sensor (not shown) embedded in flexible device body 108, for detecting the presence of unexpected moisture within the body of the device and providing or sending an alert when moisture is detected. The alert can be sent via wireless technology to a patient's wireless device (such as a tablet computer or a smartphone) or to the patient's doctor. In a further embodiment, the electronics in subcutaneous ICD 100 may include data transmission functionality via transceiver components (not shown) in the electronics. The electronics may send status data regarding the functioning of subcutaneous ICD 100, the amount of charge left in the battery, as well as patient data to a remote monitor. The transceiver components may transmit the status data via known wireless technologies such as radio frequency (herein abbreviated RF) using the 430 megahertz (herein abbreviated MHz) frequency band commonly used in medical devices, Bluetooth® or Bluetooth Smart® (low energy Bluetooth® or BLE), and the like. The remote monitor may be a wireless device owned by the patient, such as a tablet computer, a smartphone and the like, a wireless device owned by the patient's doctor, a server, an Internet site and the like. In another embodiment, subcutaneous ICD 100 may include a three axis accelerometer (not shown), for measuring ambulatory movement and electronics and circuitry (both not shown) for correlating measured ambulatory movement with heart rate acceleration of the patient in order to determine if syncope (i.e., fainting) has occurred in a patient due to an arrhythmia.

Figure 3:
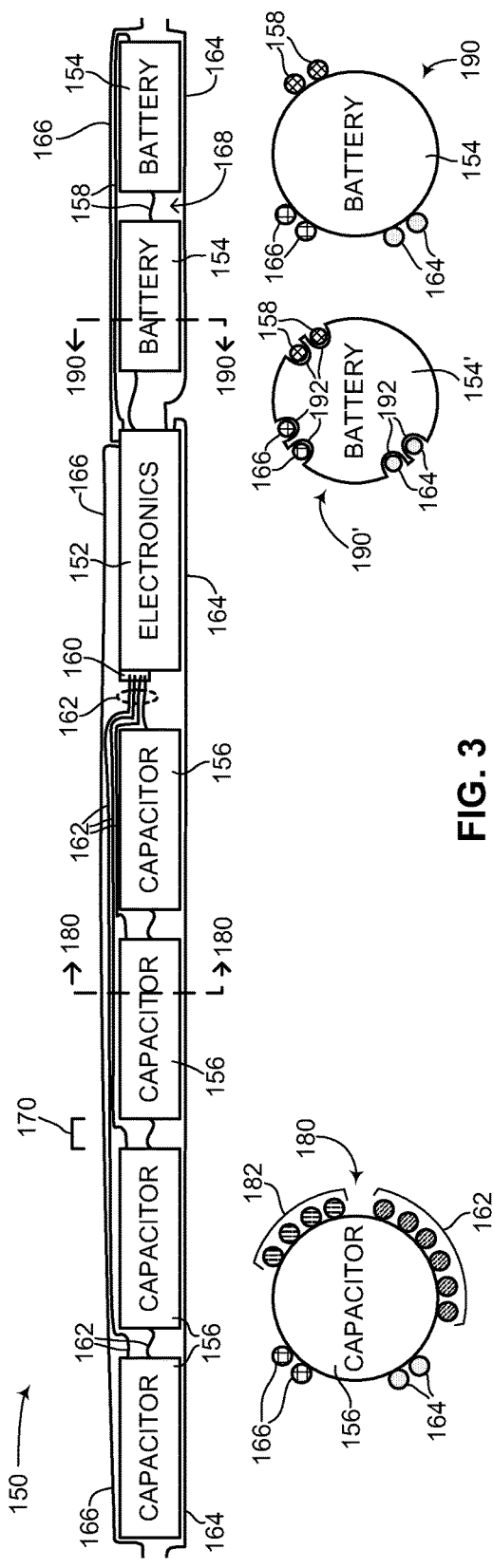
FIG. 3 is a schematic illustration of the inner components of the medical device structure of FIG. 2 including cross-section views, constructed and operative in accordance with another embodiment of the disclosed technique.

Reference is now made to FIG. 3, which is a schematic illustration of the inner components of the medical device structure of FIG. 2 including cross-section views, generally referenced 150, constructed and operative in accordance with another embodiment of the disclosed technique. As described in FIG. 2, the flexible device body of the subcutaneous ICD of the disclosed technique includes some of the main components required for a functional ICD. FIG. 3 shows those components and how they are arranged structurally. Inner components 150 include electronics 152, a plurality of batteries 154, a plurality of capacitors 156 as well as a plurality of wires, as described below. Electronics 152 includes electronic components such as a processor, a memory, a transmitter, a receiver and/or a transceiver and the like (all not shown), as described above. As shown, electronics 152 is a single inner component, however electronics 152 can also be embodied as a plurality of inner components. For example, electronics 152 in FIG. 3 could be split up into three smaller inner components containing various electronics. Electronics 152 also includes a capacitor connector 160, for coupling plurality of capacitors 156 in parallel with electronics 152. Plurality of batteries 154 are coupled in series with electronics 152 via a plurality of wires 158. It is noted that plurality of batteries 154 could also be coupled in parallel with electronics 152 (not shown). Plurality of capacitors 156 is coupled in parallel with capacitor connector 160 via a plurality of wires 162. It is noted that the coupling of the components in FIG. 3 as shown is merely brought as an example. Other configurations are possible. For example, the coupling of the inner components in FIG. 3 may be dynamic, such that inner components are coupled in parallel when the subcutaneous ICD is substantially idle and merely listening to signals for a potential arrhythmia, whereas the coupling changes to a series coupling, when plurality of capacitors 156 are being charged for delivering an electrical shock, in order to increase the voltage supplied to the capacitors. In another embodiment, plurality of capacitors 156 may be embodied as an array of capacitors coupled in series (not shown). Sensing rings (not shown) from both leads (not shown) are coupled with electronics 152 via a plurality of wires 164, whereas electrical impulse delivery electrodes (not shown) from both leads are coupled with electronics 152 via a plurality of wires 166. In another embodiment of the disclosed technique, inner components 150 may include electronics 152, at least one battery (not shown) and at least one high voltage capacitor (not shown). Plurality of capacitors 156 may include low voltage as well as high voltage capacitors.

Inner components 150 are arranged in a linear fashion, with similar components being positioned in a sequential manner, along the length of the device body (not shown). As shown, plurality of capacitors 156 includes four capacitors positioned one after the other, followed by electronics 152 and then plurality of batteries 154, which includes two batteries positioned one after the other. Such a configuration may minimize the length and number of electrical connectors (not shown) between inner components 150, thereby simplifying design and manufacturing, and also increasing the reliability of inner components 150. It is noted that other arrangements of the particular components shown are possible and are a matter of design choice, provided that inner components 150 are arranged in a linear fashion. In addition, the specific number of capacitors, batteries and electronics shown in FIG. 3 are merely brought as an example, as the specific number of each type of inner component is a design choice. The inner components of FIG. 3 could include only one battery, five capacitors and three electronics as another example. Each of electronics 152, plurality of batteries 154 and plurality of capacitors 156 has a cylindrical shape of substantially equal diameter. Electronics 152, plurality of batteries 154 and plurality of capacitors 156 are not placed flush against one another but are positioned having a gap 170, which can measure, for example, 5 millimeters (herein abbreviated mm). As described below, gap 170 enables the device body of the subcutaneous ICD of the disclosed technique a degree of flexibility. A tension member (not shown) may be placed between components, such as in gap 170, to limit the maximum possible space between components, however the tension member is not required in this embodiment.

Inner components 150 are coupled with one another via electrical wires, such as plurality of wires 158 and 162. Wires connecting adjacent components may be placed in the space between components, such as gap 170, with ample slack to enable sufficient bending between adjacent components. Wires not connecting adjacent components are run on the outer surface of components or within manufactured grooves or recesses on the outer surface of components. A cross-sectional view 180 shows the cross-section of one of plurality of capacitors 156 along with wires from non-adjacent components. As seen in this view, capacitor 156 has a circular cross-section with a plurality of wires being run along its outer surface. As seen, six wires from plurality of wires 162 are on the outer surface, coupling plurality of capacitors 156 in parallel with electronics 152. Two wires from plurality of wires 164 and two wires from plurality of wires 166 are also on the outer surface, passing over capacitor 156 and respectively coupling sensing rings (not shown) and an electrical impulse delivery electrode (not shown) from a first lead (not shown) with electronics 152. An additional set of wires 182 is shown running over the outer surface of capacitor 156, for providing charge from plurality of batteries 154 to plurality of capacitors 156. It is noted that plurality of wires 158, 162, 164, 166 and 182 are sized appropriately for the amount of current and voltage they are required to carry. It is also noted that the specific number of wires shown in FIG. 3 are merely brought as an example of how inner components 150 can be wired together. It is further noted that plurality of wires 158, 162, 164, 166 and 182 and electronics 152 can be embodied as flexible circuits.

A cross-sectional view 190 shows the cross-section of one of plurality of batteries 154 along with wires from non-adjacent components. As seen in this view, battery 154 has a circular cross-section with a plurality of wires being run along its outer surface. Two wires from plurality of wires 158 are on the outer surface, coupling plurality of batteries 154 in series with electronics 152. Two wires from plurality of wires 164 and two wires from plurality of wires 166 are also on the outer surface, passing over battery 154 and respectively coupling sensing rings (not shown) and an electrical impulse delivery electrode (not shown) from a second lead (not shown) with electronics 152. A cross-sectional view 190' shows the cross-section of another embodiment of the plurality of batteries, shown as a battery 154' along with wires from non-adjacent components. Battery 154' is fabricated to include a plurality of recesses, grooves or channels 192 into which wires from non-adjacent components can be threaded through. As shown, plurality of wires 158, 164 and 166 run on the outer surface of battery 154' through plurality of channels 192. This embodiment allows for a more compact threading of wires coupling the various inner components of the device body although also requires each of inner components 150 to be manufactured with channels or grooves on their outer surfaces. Plurality of wires 158, 162, 164, 166 and 182 may have a round, oval (not shown) or flat (not shown) cross-section. Groups of wires may be braided together to form a cable-like structure. For example, plurality of wires 164 or plurality of wires 182, as shown in cross-sectional view 180, may each be braided together to form cable-like structures. Such cable-like structures can also be embodied as flexible circuits.

Figure 4A:
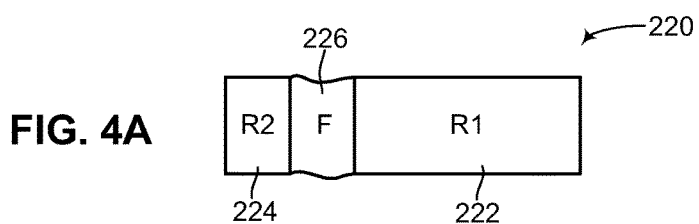
FIG. 4A is a schematic illustration of a single outer unit of the medical device structure of FIG. 2, constructed and operative in accordance with a further embodiment of the disclosed technique.
Figure 4B:
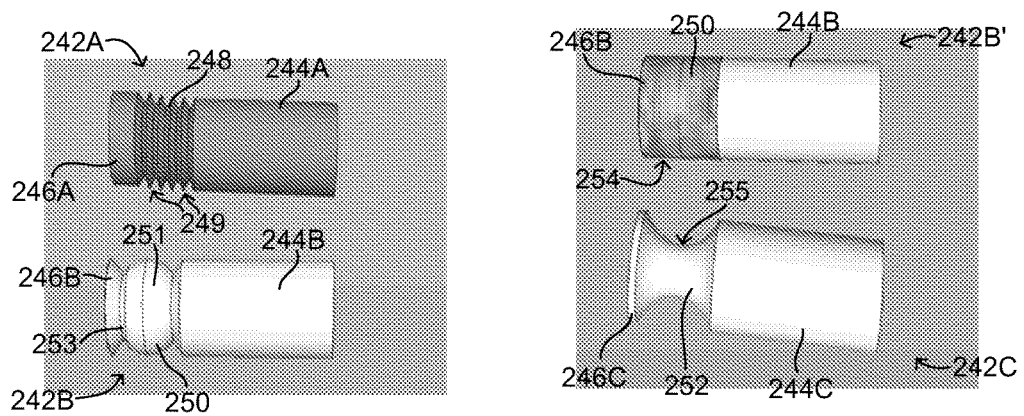
FIG. 4B is a schematic illustration showing various design embodiments of the single outer unit of FIG. 4A, constructed and operative in accordance with another embodiment of the disclosed technique.
Figure 4C:
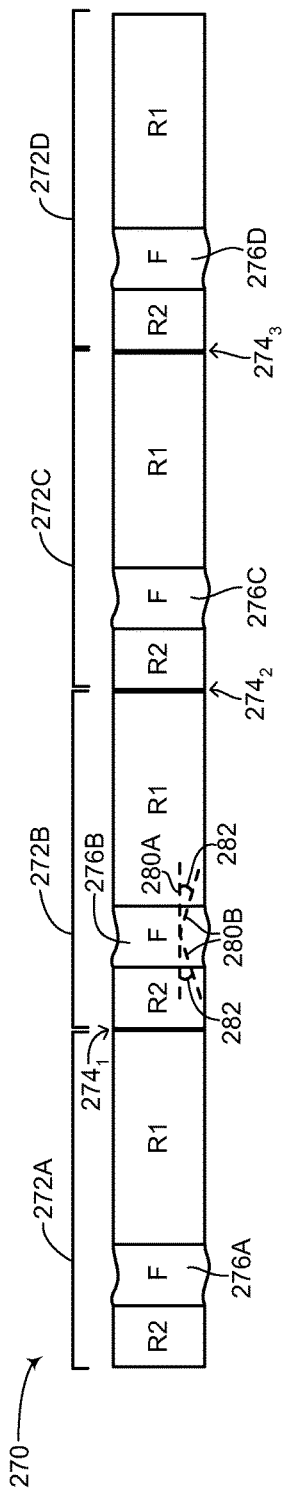
FIG. 4C is a schematic illustration showing a chain of outer units of the medical device structure of FIG. 2 coupled together, constructed and operative in accordance with a further embodiment of the disclosed technique.
Figure 4D:
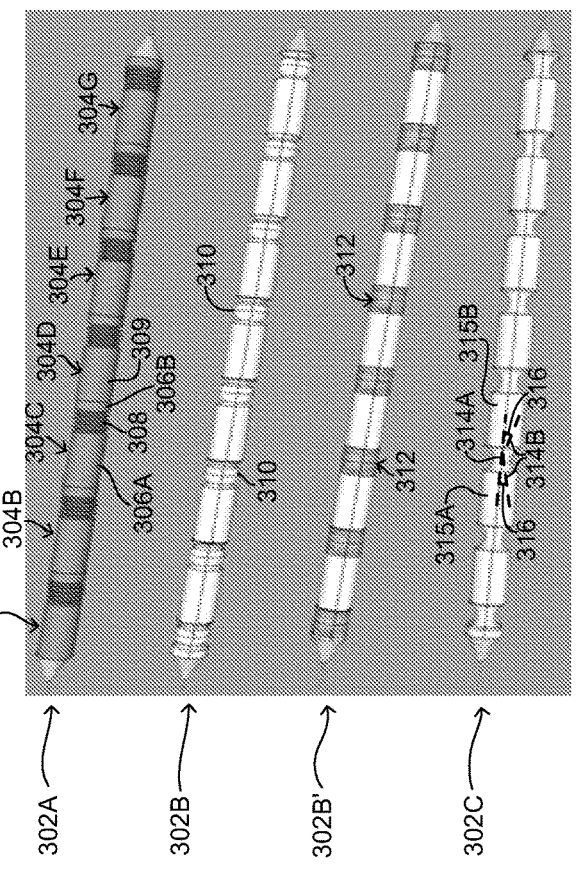
FIG. 4D is a schematic illustration showing various design embodiments of the chain of outer units of FIG. 4C, constructed and operative in accordance with another embodiment of the disclosed technique.

As described above, flexible device body 108 (FIG. 2) includes two main sections, an inner components section as described above in FIG. 3 and an outer units section. The outer units section substantially provides encasing and protection of the inner components. The outer units section includes a plurality of outer units which are coupled one to another, with each outer unit substantially encasing and protecting a single inner component, such as a battery, capacitor or electronics. FIGS. 4A and 4B show individual outer units whereas FIGS. 4C and 4D show a plurality of outer units coupled together, thus forming an outer units section as described in FIG. 2.

Reference is now made to FIG. 4A, which is a schematic illustration of a single outer unit of the medical device structure of FIG. 2, generally referenced 220, constructed and operative in accordance with a further embodiment of the disclosed technique. In one embodiment (as shown in FIG. 4A) outer unit 220 includes three elements, a first rigid element 222 (marked as R1 in FIG. 4A), a second rigid element 224 (marked as R2 in FIG. 4A) and a flexible element 226 (marked as F in FIG. 4A). Flexible element 226 is sandwiched between first rigid element 222 and second rigid element 224. Flexible element 226 allows outer unit 220 a degree of flexibility and bend angle between first rigid element 222 and second rigid element 224. The degree of flexibility can be determined according to the structure of flexible element 226 (as described in greater detail below in FIG. 4B) and may be limited by a mechanical structure (not shown). The degree of flexibility of flexible element 226 is also determined by a number of factors, such as:

the length of flexible element 226;
the diameter of flexible element 226; and
the thickness of the metal used to make flexible element 226.

The length of flexible element 226 is a design choice which depends on the requirements of a subcutaneous IMD. First rigid element 222 and second rigid element 224 substantially protect and shield the inner component (not shown) placed therein. Each of first rigid element 222, second rigid element 224 and flexible element 226 is cylindrical in shape and hollow, all having substantially the same diameter and being larger than the diameter of an inner component. The hollow nature of outer unit 220 allows an inner component and accompanying wiring to be inserted therein. The exterior surfaces of first rigid element 222 and second rigid element 224 are substantially smooth. In general, first rigid element 222 is longer than second rigid element 224 (as shown in FIG. 4A), as first rigid element 222 is principally designed to encase an inner component whereas second rigid element 224 is principally designed to enable cables and wiring to be coupled between inner components during the method of assembly as described below in FIGS. 14A-14C.

First rigid element 222 and second rigid element 224 are made from a smooth hard and preferably biocompatible metal such as stainless steel or titanium. Flexible element 226 can be made from a smooth hard metal such as stainless steel or titanium or from a biocompatible coated alloy, such as gold plated nickel. Flexible element 226 can also be made from an electrodeposited metal such as nickel or gold. Outer unit 220 is made by coupling first rigid element 222 and second rigid element 224 to flexible element 226. The rigid elements can be coupled with the flexible element by welding, soldering or by adhering the elements together using an epoxy. A polymer fill or a thin metal cover (both not shown), described below in greater detail in FIGS. 6A-6C, may cover flexible element 226, providing the exterior surface of flexible element 226 with a smooth outer surface. This is important in preventing tissue growth in flexible element 226, thus making the removal of a subcutaneous IMD easier and less painful to a patient.

Reference is now made to FIG. 4B, which is a schematic illustration showing various design embodiments of the single outer unit of FIG. 4A, generally referenced 240, constructed and operative in accordance with another embodiment of the disclosed technique. Three main embodiments of outer unit 220 (FIG. 4A) are shown in FIG. 4B, an accordion or bellows shaped outer unit 242A, a ball-and-socket shaped outer unit 242B and an hourglass shaped outer unit 242C. A modified ball-and-socket shaped outer unit 242B' is also shown. The main difference between outer units 242A, 242B and 242C is the nature of the flexible element. Accordion shaped outer unit 242A includes a first rigid element 244A, a second rigid element 246A and a flexible element 248. Flexible element 248 has an accordion or bellows shape and includes a plurality of pleats 249. Ball-and-socket shaped outer unit 242B includes a first rigid element 244B, a second rigid element 246B and a flexible element 250. Flexible element 250 is a ball-and-socket joint and includes a ball 253 which fits into a socket 251. Ball 253 is hollow (not shown) thus allowing wires to be passed there through. Hourglass shaped outer unit 242C includes a first rigid element 244C, a second rigid element 246C and a flexible element 252. Flexible element 252 has an hourglass shape and is hollow. The hourglass shape is made from a thin metal such as titanium, and includes a bend limiting structure (not shown in FIG. 4B but shown in more detail below in FIG. 6C) which is coupled with the hourglass shape and which extends toward the narrowest part of the hourglass shape. The bend limiting structure limits the travel distance of the hourglass shape and prevents the hourglass shape from extending beyond the yield strength of the thin metal. This in turn prevents kinking in the hourglass shape. A narrowest section 255 of flexible element 252 is large enough to accommodate a plurality of wires. Modified ball-and-socket shaped outer unit 242B' is substantially similar to ball-and-socket shaped outer unit 242B, and includes first rigid element 244B, second rigid element 246B and flexible element 250. Modified ball-and-socket shaped outer unit 242B' also includes a foil 254 which covers flexible element 250. Foil 254 may be a metal foil, a thin metal sleeve, a thin polymer film or a combination of such elements. Foil 254 covers and protects flexible element 250 yet is flexible enough to not reduce the flexibility of flexible element 250. Foil 254 is also used to prevent bodily tissue from growing in flexible element 250, thus making the removal of a subcutaneous ICD made from multiple outer units 242B' (not shown) easier. A similar foil can be used to cover flexible elements 248 and 252, as described in greater detail below in FIGS. 6A-6C. Each of flexible elements 248, 250 and 252 enables the first rigid element to bend with respect to the second rigid element in a plurality of planes (not shown) and not just in a single plane (not shown).

As shown, each outer unit in FIG. 4B enables the first rigid element and the second rigid element to bend at the flexible element, whether the flexible element is a set of pleats, a ball-and-socket joint or an hourglass connection. The design embodiments shown in FIG. 4B are merely examples of embodying outer unit 220 (FIG. 4A). Other designs are possible and within the scope of the disclosed technique provided they meet the requirements of outer unit 220. Each of flexible elements 248, 250 and 252 may be limited either mechanically, structurally or both, to allow for a maximum bend angle between the first rigid element and the second rigid element. For example, flexible elements 248, 250 and 252 may be limited mechanically by a structure (not shown), such as a bar or wire placed inside, over or around flexible elements 248, 250 and 252 such that the bend angle afforded by these flexible elements does not exceed a predefined maximum bend angle, such as 30 degrees. Flexible elements 248, 250 and 252 may also be limited structurally based on the thickness and rigidity of the material they are made from without the need for an additional limiting structure. For example, if plurality of pleats 249 is made from a metal, the thickness of the metal can limit the bend angle which plurality of pleats 249 can bend to. According to the design embodiments shown in FIG. 4B, a single outer unit includes a first rigid element coupled with a flexible element which is then coupled with a second rigid element. According to another embodiment of the disclosed technique, a single outer unit may include only a rigid element and a flexible element (not shown). In addition, all of the flexible elements shown in FIG. 4B are designed to provide structural integrity against a pull force of up to 10 pounds applied to the device body (such as flexible device body 108 in FIG. 2) along its axis without the use of an inner tension wire. This is a matter of design choice, dependent on the material size, strength and thickness used to produce the outer units.

Reference is now made to FIG. 4C, which is a schematic illustration showing a chain of outer units of the medical device structure of FIG. 2 coupled together, generally referenced 270, constructed and operative in accordance with a further embodiment of the disclosed technique. FIG. 4C shows a plurality of single outer units, such as outer units 272A, 272B, 272C and 272D, coupled sequentially one after the other. Each one of outer units 272A-272D is substantially similar to outer unit 220 (FIG. 4A) and includes a first rigid element (not labeled although shown as R1), a flexible element (shown as F) and a second rigid element (not labeled although shown as R2). For example, outer unit 272A includes flexible element 276A, outer unit 272B includes flexible element 276B, outer unit 272C includes flexible element 276C and outer unit 272D includes flexible element 276D. The outer structure of a subcutaneous ICD according to the disclosed technique is formed by coupling outer units sequentially with the first rigid element of one outer unit being coupled with the second rigid element of a subsequent outer unit. For example, as shown in FIG. 4C, outer unit 272A is coupled with outer unit 272B by coupling the first rigid element of outer unit 272A with the second rigid element of outer unit 272B, as shown by an arrow $274_1$. Outer unit 272B is coupled with outer unit 272C by coupling the first rigid element of outer unit 272B with the second rigid element of outer unit 272C, as shown by an arrow $274_2$, and outer unit 272C is coupled with outer unit 272D by coupling the first rigid element of outer unit 272C with the second rigid element of outer unit 272D, as shown by an arrow $274_3$. In this manner, the outer structure of a device body can be formed for a subcutaneous IMD as constructed according to the disclosed technique. Each of flexible elements 276A-276D enables chain of outer units 270 a degree of overall flexibility. As shown, for example, depending on a number of factors as listed above, flexible element 276B may have a bend angle 282 defined between a horizontal line 280A and two lines 280B representing the axes along which the rigid elements (not labeled) of outer unit 272B can maximally be bent to. It is noted that the bend angle of a given outer unit may be different than the bend angle of another outer unit. For example, the bend angles afforded by flexible elements 276A-276D may each be substantially the same, different or a combination in between, with some outer units having the same bend angle while others have a different bend angle. It is also noted that based on this structure and due to the circular nature of the outer units and how they are coupled, the bend angle of chain of outer units 270 is not limited to a two dimensional surface but rather can bend freely in three dimensional space.

Reference is now made to FIG. 4D, which is a schematic illustration showing various design embodiments of the chain of outer units of FIG. 4C, generally referenced 300, constructed and operative in accordance with another embodiment of the disclosed technique. A chain of outer units 302A is constructed from a plurality of accordion shaped outer units coupled sequentially, where each accordion shaped outer unit is substantially similar to accordion shaped outer unit 242A (FIG. 4B). A chain of outer units 302B is constructed from a plurality of ball-and-socket shaped outer units coupled sequentially, where each ball-and-socket shaped outer unit is substantially similar to ball-and-socket shaped outer unit 242B (FIG. 4B). A chain of outer units 302C is constructed from a plurality of hourglass shaped outer units coupled sequentially, where each hourglass shaped outer unit is substantially similar to hourglass shaped outer unit 242C (FIG. 4B). A chain of outer units 302B' is constructed from a plurality of modified ball-and-socket shaped outer units coupled sequentially, where each modified ball-and-socket shaped outer unit is substantially similar to modified ball-and-socket shaped outer unit 242B (FIG. 4B).

As shown in chain of outer units 302A, seven accordion shaped outer units 304A-304G are coupled sequentially, thus forming the outer structure of a device body, with the second rigid element of a first outer unit being coupled with the first rigid element of a second outer unit. As an example, accordion shaped outer unit 304C includes a first rigid element 306A, a flexible element 308 and a second rigid element 306B and accordion shaped outer unit 304D includes a first rigid element 309. Outer unit 304C is coupled with outer unit 304D by coupling second rigid element 306B to first rigid element 309. Chain of outer units 302B includes seven ball-and-socket shaped outer units (not labeled) coupled sequentially, each outer unit including a flexible element 310, and chain of outer units 302B' includes seven modified ball-and-socket shaped outer units (not labeled) coupled sequentially, each flexible element of each outer unit being covered by a foil 312. Chain of outer units 302C shows a bending angle 316 between a first outer unit 315A and a second outer unit 315B. Bending angle 316 is formed between a horizontal line 314A and maximal bending axes afforded by the flexible element (not labeled) between first outer unit 315A and second outer unit 315B, delineated by lines 314B.

Figure 5:
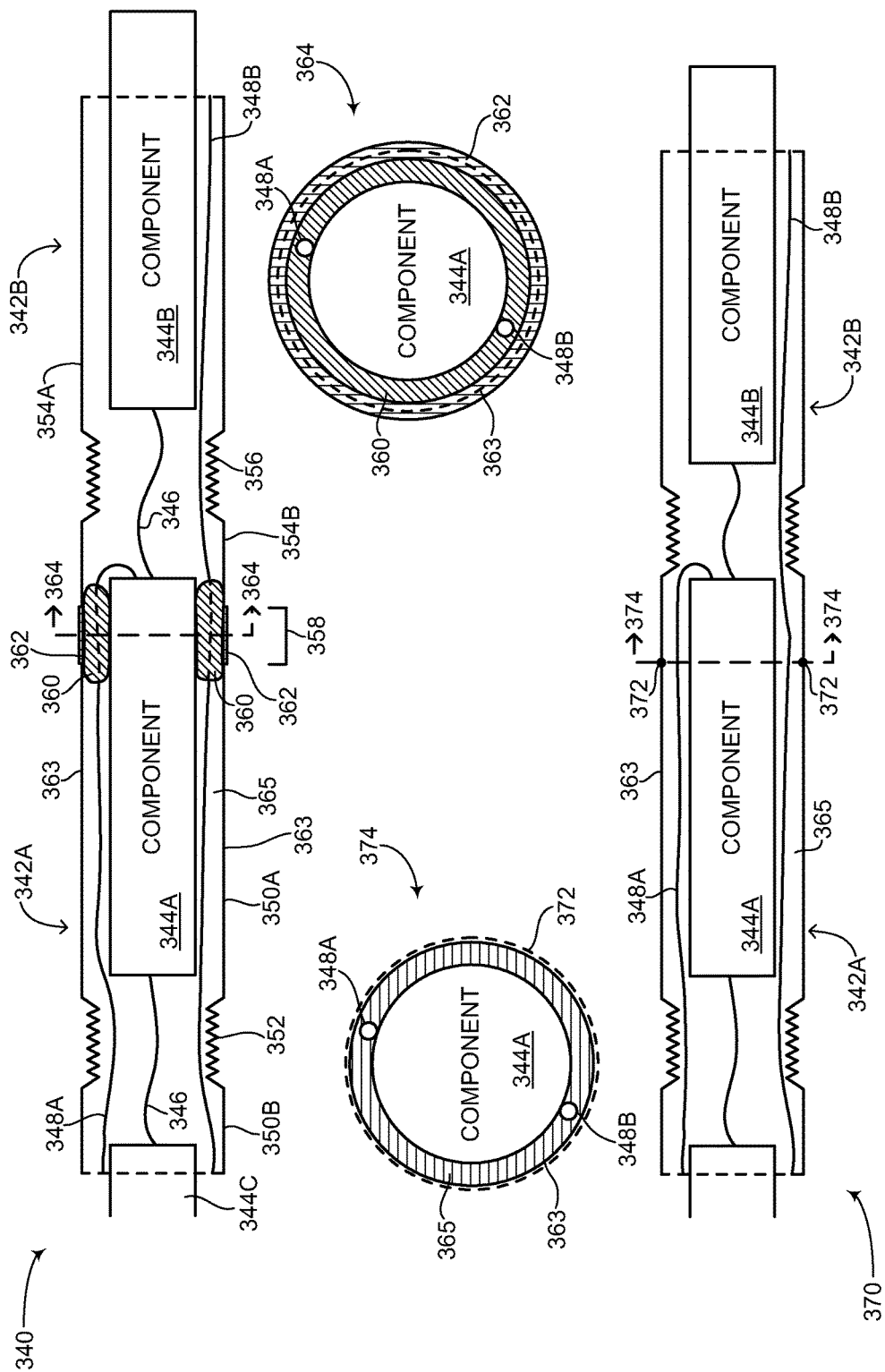
FIG. 5 is a schematic illustration showing different embodiments for coupling a first outer unit to a second outer unit including cross-section views, constructed and operative in accordance with a further embodiment of the disclosed technique.

Reference is now made to FIG. 5, which is a schematic illustration showing different embodiments for coupling a first outer unit to a second outer unit including cross-section views, generally referenced 340 and 370, constructed and operative in accordance with a further embodiment of the disclosed technique. FIGS. 4C and 4D above showed multiple outer units coupled to one another but did not show how such a coupling is executed. This is shown in FIG. 5, which also shows the positioning of inner components within the outer units. Shown in a first embodiment 340 for coupling two outer units together, is a first outer unit 342A and a second outer unit 342B. First outer unit 342A includes a first rigid element 350A, a flexible element 352 and a second rigid element 350B, and second outer unit 342B includes a first rigid element 354A, a flexible element 356 and a second rigid element 354B. To demonstrate the disclosed technique, flexible elements 352 and 356 are shown having an accordion shape, however any of the previously disclosed embodiments for the flexible element, as shown above in FIG. 4B, could have been used for flexible elements 352 and 356.

As shown, a first inner component 344A is placed inside first outer unit 342A and a second inner component 344B is placed inside second outer unit 342B. A portion of a third inner component 344C is also shown. Inner components 344A-344C each have a cylindrical shape and may be batteries, capacitors or electronics, as described above in FIG. 2. The diameter (not shown) of the outer units is sufficiently large to accommodate the diameter (not shown) of the inner components as well as any wires which couple between inner components and other elements of the subcutaneous IMD of the disclosed technique. First inner component 344A is positioned in first outer unit 342A such that a majority portion of it is positioned in first rigid element 350A, whereas a minority portion of it is positioned in second rigid element 354B. The same kind of positioning is used for second inner component 344B and third inner component 344C. Inner components are thus placed in the rigid elements of an outer unit and not in the flexible elements of those outer units. This positioning enables the flexible elements to bend without hindrance from the inner components. As shown schematically, a plurality of wires are also located within outer units 342A and 342B, depending on how the inner components are to be coupled (e.g., in series, in parallel and the like). For example, a plurality of wires 346 electrically couples first inner component 344A to both second inner component 344B and third inner component 344C in series. A wire 348A electrically couples first inner component 344A with another inner component or element, such as a sensing ring (not shown) or an electrical impulse delivery electrode (not shown), whereas a wire 348B runs along the length of the inner components yet is coupled with none of them. The plurality of wires is shown positioned with ample slack such that the wires will not be under stress or tension if the flexible elements of the outer units bend.

As described in greater detail below in FIGS. 14A-14C, the device body of a subcutaneous IMD constructed according to the disclosed technique is assembled one outer unit at a time. Thus in FIG. 5, third inner component 344C is first electrically coupled with first inner component 344A, and then first outer unit 342A is placed over first inner component 344A. Wires 348A and 348B are thread through first outer unit 342A and first outer unit 342A is then coupled with the outer unit (not shown) encasing third inner component 344C. Second inner component 344B is then first electrically coupled with first inner component 344A, for example by coupling the two inner components via one of plurality of wires 346, and then second outer unit 342B is placed over second inner component 344B. Wire 348B is thread through second outer unit 342B. In first embodiment 340, first outer unit 342A and second outer unit 342B are positioned such that there is a gap 358 between them; they thus do not touch one another directly. Gap 358 may measure 1-2 mm or less and is as small as possible. An epoxy 360 is then inserted into gap 358 to couple first outer unit 342A with second outer unit 342B. Epoxy 360 substantially fills the entire space of gap 358 and may extend laterally beyond the specific dimensions of gap 358. Epoxy 360 may be a biocompatible epoxy, such as silicone, polyurethane, Hysol® or a thermoset epoxy. Epoxy 360 may substantially anchor first inner component 344A to an outer surface 363 of first outer unit 342A such that first inner component 344A does not move around once placed inside first outer unit 342A. Epoxy 360 may also anchor and hold wires 348A and 348B. An interior 365 of first outer unit 342A may remain filled with an inert gas or may be filled with an epoxy as well (not shown). Interior 365 may also be partially filled with a desiccant (not shown) to prevent shorting or aching inside first outer unit 342A. In an embodiment where an inert gas is used to fill interior 365, epoxy 360 is not placed continuously around first inner component 344A in order to allow the inert gas to freely flow between outer units. In this embodiment, one of the outer units may include a fill port (not shown), for example on its side, for inserting the inert gas into interior 365. Once filled with the inert gas, the fill port is then welded shut. Once epoxy 360 is dry, the exterior surface of epoxy 360, which couples first outer unit 342A with second outer unit 342B, is covered by a thin layer 362. Thin layer 362 may be a thin metal layer, such as platinum, stainless steel, titanium or gold, which is sputtered over the exterior surface of epoxy 360. Thin layer 362 may also be a metal-filled epoxy. In such an embodiment, the metal-filled epoxy requires a high percent by weight, for example, more than 75% of a conductive metal, such as silver. In either embodiment, thin layer 362 acts as an additional moisture barrier and as an electromagnetic shield over the exterior surface of epoxy 360. Accordingly, first outer unit 342A is coupled with second outer unit 342B using epoxy 360 and thin layer 362. Thin layer 362 may be partially flexible.

A cross-section view of the coupling of outer units in first embodiment 340 is shown delineated by an arrow 364. As shown in cross-section view 364, first inner component 344A has a circular cross-section and is surrounded by epoxy 360, which also anchors wires 348A and 348B. In gap 358, epoxy 360 is then surrounded by thin layer 362. The outline of outer surface 363 of first outer unit 342A is shown as a dashed line. It is noted that in this embodiment, where two outer units are coupled together using an epoxy, each outer unit may include a moisture sensor (not shown) for detecting any fluids leaking into an individual outer unit.

A second embodiment 370 for coupling two outer units together is also shown in FIG. 5, with equivalent numbering used to show equivalent elements. In this embodiment, first outer unit 342A is coupled with second outer unit 342B by welding the two outer units together once the inner components are electrically coupled and positioned within respective outer units. A weld joint 372 is shown coupling first outer unit 342A with second outer unit 342B. There is thus no gap between first outer unit 342A and second outer unit 342B. In this embodiment, the interior of each outer unit, such as interior 365, may be filled with an epoxy (not shown) for anchoring the inner component and wires placed within each outer unit, a polymer (not shown) which will harden upon exposure to moisture, or filled with an inert gas, such as argon or nitrogen. The interior of each outer unit may also include a desiccant. A cross-section view of the coupling of outer units in second embodiment 370 is shown delineated by an arrow 374. As shown in cross-section view 374, first inner component 344A has a circular cross-section and is surrounded by interior 365, which may be filled with an epoxy, polymer or may be an inert gas. Wires 348A and 348B surround first inner component 344A. Outer surface 363 of first outer unit 342A is shown surrounded by weld joint 372, which is shown as a dashed line.

Other methods for coupling sequential outer units together are possible. For example, outer units may be coupled by soldering, brazing or by the use of an adhesive. The device body of a subcutaneous IMD of the disclosed technique is thus constructed of a plurality of outer units sequentially coupled to one another wherein each outer unit encases a respective inner component and any accompanying wiring.

Figure 6A:
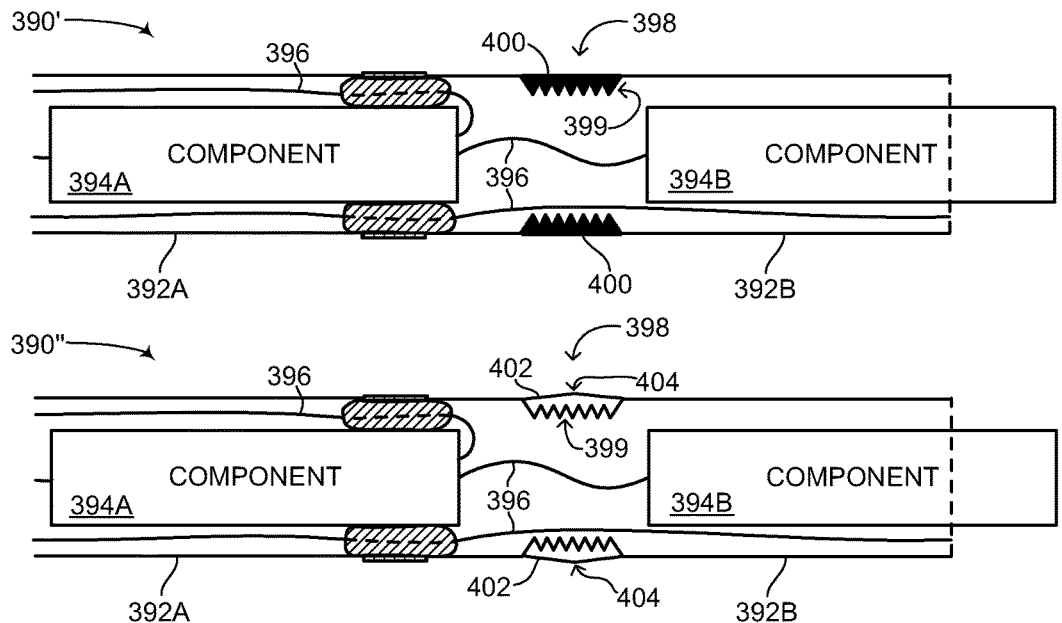
FIG. 6A is a schematic illustration showing different embodiments for covering the flexible section of a first outer unit design, constructed and operative in accordance with another embodiment of the disclosed technique.
Figure 6B:
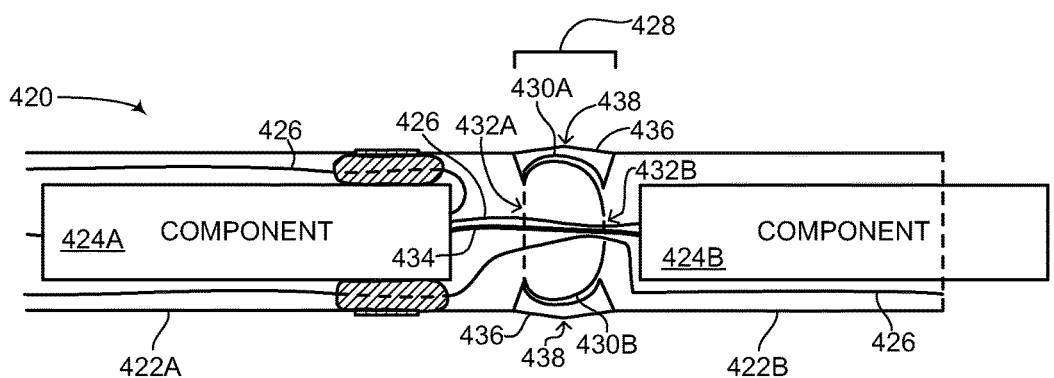
FIG. 6B is a schematic illustration showing an embodiment for covering the flexible section of a second outer unit design, constructed and operative in accordance with a further embodiment of the disclosed technique.

As mentioned above, the outer units of the device body each include a flexible element. Each flexible element should be covered in order to give the exterior surface of the device body a smooth finish, thus easing implantation of the device body into a patient and also to prevent bodily tissue growth within each flexible element, thus easing removal of the device body if needed. FIG. 4B above showed various embodiments of outer units according to the disclosed technique. FIGS. 6A-6C below show various embodiments for covering the various flexible elements of the different outer unit embodiments shown above. Reference is now made to FIG. 6A, which is a schematic illustration showing different embodiments for covering the flexible section of a first outer unit design, generally referenced 390' and 390", constructed and operative in accordance with another embodiment of the disclosed technique. Embodiments 390' and 390" relate to an outer unit having an accordion shaped flexible element, as shown above in FIG. 4B, including a plurality of pleats 399. Equivalent elements in embodiments 390' and 390" are labeled using equivalent numbering.

In embodiment 390' a first outer unit 392A is coupled with a second outer unit 392B using an epoxy and a thin layer (both not labeled). First outer unit 392A encases a first inner component 394A and second outer unit 392B encases a second inner component 394B. A plurality of wires 396 may couple the inner components together and may couple the inner components with other elements (not shown). Second outer unit 392B includes a flexible element 398. Flexible element 398 is covered by a polymer 400, which substantially fills in the bends and folds of plurality of pleats 399 of flexible element 398. Polymer 400 enables flexible element 398 to bend. Polymer 400 may be for example silicone, Parylene, polyurethane or polytetrafluoroethylene (herein abbreviated PTFE). Polymer 400 is in the form of a sheet or tube which is attached to either side of flexible element 398 with a biocompatible adhesive such as silicone rubber or a polyurethane adhesive.

In embodiment 390", flexible element 398 is covered by a thin metal covering 402, which substantially covers flexible element 398. Thin metal covering 402 may extend in length beyond the length of flexible element 398. Thin metal covering 402 may be made from a thin metal foil of titanium or gold, or from an alloy of those metals. Thin metal covering 402 may include a bend 404 to enable flexible element 398 to bend. Bend 404 may be a fold or a kink in thin metal covering 402. The length of thin metal covering 402 and the amount of bending in bend 404 may be used to limit the flexibility of flexible element 398.

Reference is now made to FIG. 6B, which is a schematic illustration showing an embodiment for covering the flexible section of a second outer unit design, generally referenced 420, constructed and operative in accordance with a further embodiment of the disclosed technique. Embodiment 420 relates to an outer unit having a ball-and-socket joint as its flexible element, as shown above in FIG. 4B. In embodiment 420, a first outer unit 422A is coupled with a second outer unit 422B using an epoxy and a thin layer (both not labeled). First outer unit 422A encases a first inner component 424A and second outer unit 422B encases a second inner component 424B. A plurality of wires 426 may electrically couple the inner components together and may couple the inner components with other elements (not shown). Second outer unit 422B includes a flexible element 428, which includes a socket 430A and a ball 430B. Socket 430A is slightly larger than ball 430B. In order to prevent ball 430B from dislocating from socket 430A, a safety cable 434 may structurally couple first inner component 424A with second inner component 424B. Safety cable 434 may be placed on or near a center line (not shown) of first inner component 424A and second inner component 424B. Safety cable 434 may also be used to prevent ball 430B and socket 430A from overextending. Ball 430B is hollow, having a first opening 432A and a second opening 432B. Both first opening 432A and second opening 432B are wide enough to enable plurality of wires 426 and safety cable 434 to pass there through between outer units. Flexible element 428 is covered by a thin metal covering 436, which substantially covers flexible element 428. Thin metal covering 436 may extend in length beyond the length of flexible element 428. Thin metal covering 436 is substantially similar to thin metal covering 402 (FIG. 6A). Thin metal covering 436 may also be embodied as foil 254 (FIG. 4B). Thin metal covering 436 may include a bend 438 to enable flexible element 428 to bend. Bend 438 may be a fold or a kink in thin metal covering 436. The length of thin metal covering 436 and the amount of bending in bend 438 may be used to limit the flexibility of flexible element 428.

Reference is now made to FIG. 6C, which is a schematic illustration showing an embodiment for covering the flexible section of a third outer unit design, generally referenced 460, constructed and operative in accordance with another embodiment of the disclosed technique. Embodiment 460 relates to an outer unit having an hourglass shape as its flexible element, as shown above in FIG. 4B. In embodiment 460, a first outer unit 462A is coupled with a second outer unit 462B by using an epoxy or by being welded together (both not labeled). First outer unit 462A encases a first inner component 464A and second outer unit 462B encases a second inner component 464B. A plurality of wires 466 may electrically couple the inner components together and may couple the inner components with other elements (not shown). Second outer unit 462B includes a flexible element 468, which has an hourglass shape. The hourglass shape of flexible element 468 creates a cavity 472 in which bodily tissue growth can occur. Cavity 472 is filled in using a polymer 474. Polymer 474 may be a soft polymer, such as silicone, polyurethane, PTFE or other elastomeric material known to those skilled in the art, which enables cavity 472 to be filled yet still enables flexible element 468 to bend. Polymer 474 prevents bodily tissue growth within cavity 472 while also providing structural support to the hourglass shape of flexible element 468, thereby preventing kinking in the hourglass shape. Polymer 474 also makes the outer diameter (not shown) of flexible element 468 substantially the same as the outer diameter (not shown) of the rigid elements (not labeled) of second outer unit 462B. A plurality of bend limiting structures 478 may be placed in cavity 472 before it is filled with polymer 474. Plurality of bend limiting structures 478 may each be made from a metal or a hard polymer, in order to limit the bend angle of flexible element 468. The length of each one of plurality of bend limiting structures 478 can be adjusted to increase or decrease the bend angle (not shown) of flexible element 468. In general, the bend angle is limited to no more than 20 degrees so as to prevent the hourglass shape from kinking. In one embodiment of the disclosed technique, cavity 472 may include at least one bend limiting structure (not shown). Once cavity 472 is filled with polymer 474, the outer surface (not labeled) of polymer 474 may be covered with a thin layer 476. Thin layer 476 may be another polymer, a sputtered metal or a metal sleeve. As shown, flexible element 468 may be coupled with the rigid elements of second outer unit 462B by soldering or welding, shown in FIG. 6C by a plurality of lines 470.

Reference is now made to FIG. 7, which is a schematic illustration showing the interior and cross-section of the flexible device body of the medical device structure of FIG. 2, generally referenced 500, constructed and operative in accordance with a further embodiment of the disclosed technique. Flexible device body 500 has been assembled as shown previously in FIGS. 3-6C and shows how two inner components and two outer units are fully coupled and assembled. Flexible device body 500 includes a first outer unit 502A and a second outer unit 502B. First outer unit 502A includes a flexible element 510A and second outer unit 502B includes a flexible element 510B. As an example, flexible elements 510A and 510B are embodied as accordion shaped flexible elements. First outer unit 502A encases electronics 504A and second outer unit 502B encases battery 504B. Electronics 504A includes a capacitor connector 506. Electronics 504A, battery 504B and other elements of flexible device body 500 (not shown) and the medical device structure (such as sensing rings and electrical impulse delivery electrodes) are coupled via a plurality of wires 508. Some of plurality of wires 508 couple between inner components whereas other couple inner components not shown in FIG. 7. The exterior surface of each of flexible elements 510A and 510B has been filled in and covered with a polymer 512, as described above in FIG. 6A. First outer unit 502A has been coupled with second outer unit 502B by an epoxy 514, with the outer surface of epoxy 514 being covered with a thin layer 516, as described above in FIG. 5. An epoxy 522 is partially shown between first outer unit 502A and another outer unit (not shown). An outer surface of the outer units is shown by an arrow 517.

Once all inner components and outer units have been coupled together, the outer surface of the outer units, i.e., outer surface 517 of flexible device body 500, may be coated or covered with a polymer 518. Polymer 518 may be a poly(para-xylylene) polymer, such as Parylene. Polymer 518 may be any biocompatible, liquid resistant polymer. Optionally, an additional coating 520 may be placed over polymer 518. Addition coating 520 may be a polymer sleeve made from a chemically inert material, such as PTFE, for example Teflon®, expanded PTFE (ePTFE), for example Gore-Tex™, or from materials such as ethylene tetrafluoroethylene (herein referred to as ETFE), for preventing bodily tissue growth on the outer surface of flexible device body 500 and for easing in the removal of flexible device body 500 from a patient. In another embodiment of the disclosed technique, additional coating 520 may be a metal sleeve and may cover the entire outer surface of flexible device body 500 or may partially cover (not shown) the outer surface of flexible device body 500. In a further embodiment of the disclosed technique, additional coating 520 may be a metalized polymer. A cross-section view 530 shows electronics 504A and its surrounding layers. As seen, electronics 504A is surrounded by epoxy 514, which also encases plurality of wires 508. Surrounding epoxy 514 is thin layer 516, followed by polymer 518 and the optional additional coating 520. The outline of outer surface 517 is shown as a dashed line.

In the embodiment in which additional coating 520 is a metalized polymer, both polymer 518 and additional coating 520 substantially provide a hermetic seal around outer surface 517 of the outer units. A plurality of electrodes (not shown) may be placed between polymer 518 and additional coating 520, for detecting any fluid leakage into the coating of outer surface 517. The plurality of electrodes may be a plurality of sensing circuits for detecting the presence of moisture and may be coupled (not shown) with electronics 504A. In this embodiment, if additional coating 520 has a leak, the plurality of sensing circuits along with electronics 504A can be used to wirelessly alert a physician of the presence of a leak in flexible device body 500 and that the subcutaneous IMD of the disclosed technique should be changed before the actual subcutaneous IMD becomes electrically compromised. It is noted that the plurality of sensing circuits detect leakages in the rigid sections of each outer unit. As mentioned above, the outer units may be made from metal and are thus hermetically sealed in and of themselves. Thus even if additional coating 520 has a leak, the outer units may not. However, to avoid the possibility of the leak spreading and eventually making it through the hermetic seal of the outer units, since they may kink and bend over time and use, according to the disclosed technique, the plurality of sensing circuits for detecting the presence of moisture is situated between additional coating 520 and polymer 518. The physician is thus alerted to a break in the hermetic seal of additional coating 520 before there is a chance that the hermetic seal of the outer units is compromised.

Figure 8A:
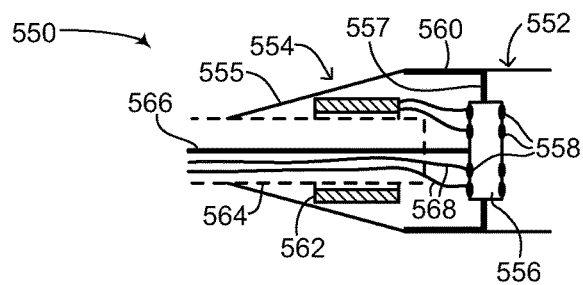
FIG. 8A is a schematic illustration showing the interior of an end coupler and strain relief of the medical device structure of FIG. 2, constructed and operative in accordance with another embodiment of the disclosed technique.
Figure 8B:
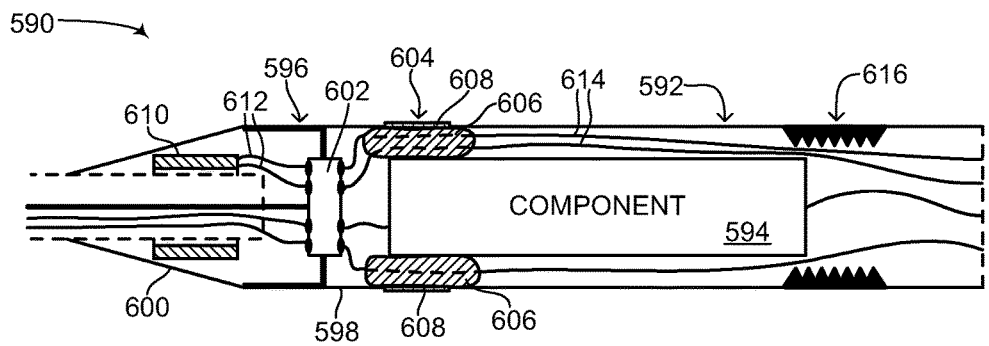
FIG. 8B is a schematic illustration showing the interior of the end coupler and strain relief of FIG. 8A coupled with an inner component and outer unit, constructed and operative in accordance with a further embodiment of the disclosed technique.

Reference is now made to FIG. 8A, which is a schematic illustration showing the interior of an end coupler and strain relief of the medical device structure of FIG. 2, generally referenced 550, constructed and operative in accordance with another embodiment of the disclosed technique. FIG. 8A shows an end coupler 552 and a strain relief 554, which together form a transition unit, as shown above in FIG. 2. End coupler 552 is substantially cylindrical in shape, is shaped like an 'H' in its cross-section and is made from the same material (such as a metal) as an outer unit (not shown), such as stainless steel or titanium. End coupler 552 may include an electrical feed-through 556 in its center, which includes a plurality of connectors 558. Electrical feed-through 556 enables wiring on the inside of a flexible device body (not shown) to be coupled with wiring outside the flexible device body, such as wiring coming from leads (not shown), as well in the opposite direction, such as wiring going to electrical impulse delivery electrodes (not shown). In general, only one electrical feed-through is required for both delivering electrical energy to electrical impulse delivery electrodes and for receiving electrical energy from sensing rings (not shown). Electrical feed-through 556 may be embodied to include at least one type of filter and may provide a dielectric barrier, a moisture barrier, electromagnetic filtering, radio frequency filtering, a hermetic seal and the like between the inside and the outside of the flexible device body. Electrical feed-through 556 may also include a passive electrical filter (not shown) for preventing large current spikes from entering the flexible device body (not shown) of the subcutaneous ICD of the disclosed technique. The electrical impulse delivery electrode (not shown) of a lead (not shown) of the disclosed technique substantially functions as an antenna when not delivering electrical impulses and can build up current if the patient passes near a magnetic, electrical or electromagnetic field (for example, an anti-theft system). The current build up may spontaneously spike and traverse down the wires coupling the electrical impulse delivery electrode with the electronics and inner components of the subcutaneous ICD, thus possibly burning out some of the inner circuitry of the subcutaneous ICD. A passive electrical filter included in electrical feed-through 556 may prevent such current spikes from entering the flexible device body of the subcutaneous ICD. The same goes for sensing rings (not shown) in the leads of the disclosed technique. Even though the current build up in sensing rings is less than in the electrical impulse delivery electrode, the sensing rings are coupled with sensitive amplifiers (not shown), located in the electronics of the flexible device body, which can easily be short-circuited by a noise spike. The passive electrical filter can thus prevent such noise spikes from entering the flexible device body and from short-circuiting the sensitive amplifiers. Electrical feed-through 556 may further include an electromagnetic (herein referred to as EM) filter, a radio frequency (herein referred to as RF) filter or both, for filtering out EM interference, RF interference or both. The EM filter, RF filter or both may be embodied as a discoidal capacitive filter. End coupler 552 or electrical feed-through 556 may also include an eyelet or hook (not shown) for coupling a safety wire 566 with the flexible device body. Safety wire 566 may also be a tension wire. Electrical feed-through 556 may be constructed as an integral part of end coupler 552 or may be constructed as a separate part which can be coupled to end coupler 552, for example by a weld, by an adhesive and the like. As shown in FIG. 8B, one end of the 'H' shape of end coupler 552 is used to close the end of a distal or proximal outer unit (not shown) of the flexible device body (not shown).

Strain relief 554 has a tapered end 555 as well as a flat end 557 and is hollow. As mentioned above, strain relief 554 substantially transitions the larger diameter of the flexible device body (not shown) to the smaller diameter of a lead 564 of the subcutaneous IMD of the disclosed technique. Strain relief 554 is open on both sides thus enabling wires to be passed there through. Strain relief 554 can be made from a biocompatible polymer such as urethane, polyurethane or silicone. Tapered end 555 tapers sufficiently to enable lead 564 to be inserted therein. Lead 564 is coupled with strain relief 554 via an adhesive, such as silicone or polyurethane. Flat end 557 is shaped to fit into one end of end coupler 552 and may be coupled with end coupler 552 via an adhesive 560. As shown, a plurality of sensing wires 568, coupled with sensors or sensing rings (both not shown) in lead 564 are coupled with plurality of connectors 558 in electrical feed-through 556. Safety wire 566, running through lead 564, is also coupled with electrical feed-through 556 and is used for securing lead 564 to the flexible device body via end coupler 552, for preventing lead 564 from detaching from the flexible device body. Strain relief 554 also includes a charging coil 562 which is coupled with electrical feed-through 556 via a plurality of wires (not labeled). Charging coil 562 enables rechargeable batteries (not shown) in the device body to be recharged inductively using an external charging device (not shown). Charging coil 562 can also be embodied as a cylindrically shaped charging antenna. In an embodiment in which the batteries are not rechargeable, the charging coils shown in FIG. 8A are not included in strain relief 554.

Reference is now made to FIG. 8B, which is a schematic illustration showing the interior of the end coupler and strain relief of FIG. 8A coupled with an inner component and outer unit, generally referenced 590, constructed and operative in accordance with a further embodiment of the disclosed technique. As shown, an outer unit 592 includes an inner component 594. A transition unit 596, which includes end coupler 598 and strain relief 600, are also shown. End coupler 598 includes an electrical feed-through 602 and strain relief 600 includes a charging coil 610. Outer unit 592 is positioned adjacent to end coupler 598 however a gap 604 is present between the two elements. Gap 604 is filled with an epoxy 606. Epoxy 606 substantially couples end coupler 598 and outer unit 592 together. Epoxy 606 also couples inner component 594 to outer unit 592 and secures a plurality of wires 614. Once epoxy 606 is dry, the outer surface of epoxy 606 is covered with a thin layer 608. Thin layer 608 may be a sputtered metal or a metal-filled epoxy, as described above in FIG. 5. As seen, the coupling of end coupler 598 to outer unit 592 is substantially similar to the coupling of two outer units together, as described above in FIG. 5. In another embodiment of the disclosed technique, end coupler 598 and outer unit 592 can be welded or soldered together (not shown). In a further embodiment of the disclosed technique, outer unit 592 may be coupled with end coupler 598 via a flexible element. For example, a flexible element 616 may be positioned at the junction between end coupler 598 and outer unit 592 (not shown). Also seen in FIG. 8B is how wires outside an outer unit are coupled with wires inside an outer unit via electrical feed-through 602. Charging coil 610 is coupled with a plurality of wires 612 to connectors (not labeled) in electrical feed-through 602. Plurality of wires 612 is coupled via electrical feed-through 602 to plurality of wires 614, which couples charging coil 610 with a plurality of batteries (not shown).

Figure 9:
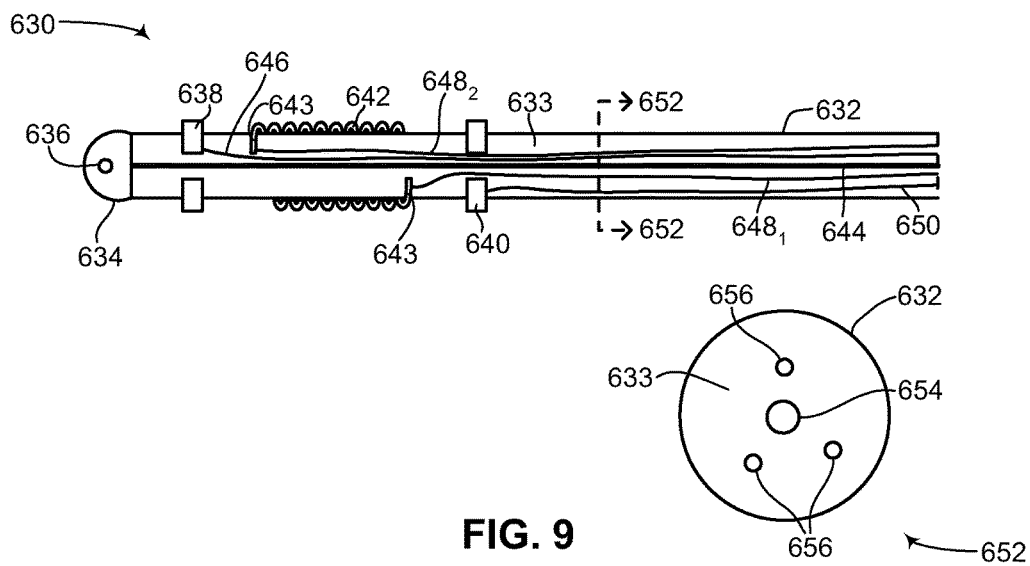
FIG. 9 is a schematic illustration showing the interior and cross-section of a lead of the medical device structure of FIG. 2, constructed and operative in accordance with another embodiment of the disclosed technique.

Reference is now made to FIG. 9, which is a schematic illustration showing the interior and cross-section of a lead of the medical device structure of FIG. 2, generally referenced 630, constructed and operative in accordance with another embodiment of the disclosed technique. As shown, lead 630 includes a tubular section 632 which substantially runs the length of lead 630. Tubular section 632 is made from a polymer such as polyurethane or silicone. If polyurethane is used then its Shore hardness should be between 80 A to 55 D. If silicone is used then its Shore hardness should be between 35 D to 35 A. At the end of tubular section 632 is a tip section 634 having a rounded end which includes a suture eyelet 636. Tip section 634 may be made from metal and may be coupled with a distal end (not labeled) of tubular section 632. Suture eyelet 636 is large enough to pass a suture through and to enable the distal end of lead 630 to be coupled with bodily tissue when lead 630 is implanted in a patient. Suture eyelet 636 can also be used when implanting the subcutaneous IMD of the disclosed technique, as a suture or thread can be affixed to suture eyelet 636 and the suture or thread can then be used to pull the subcutaneous IMD into position in a patient. Likewise, a suture or thread can be affixed to suture eyelet 636 and used to pull the subcutaneous ICD out of the patient if the implanted medical device needs to be removed. It is noted that tubular section 632 may also include at least one suture sleeve (not shown) or at least one suture anchor (not shown), for either suturing the subcutaneous IMD when implanted in the patient or for easing implantation of the subcutaneous IMD in the patient. The distal end of tubular section 632 includes a first sensing ring 638 and a second sensing ring 640. Second sensing ring 640 may be optional. Each one of first and second sensing rings may be made from a metal or alloy such as platinum, stainless steel, gold or a platinum alloy. Tubular section 632 may include additional sensing rings (not shown). As seen, first and second sensing rings 638 and 640 are positioned around tubular section 632, however they also partially penetrate tubular section 632. First and second sensing rings are used for sensing electrical activity of the heart (not shown) and are thus positioned on the outer surface of tubular section 632. Between first and second sensing rings 638 and 640 is an electrical impulse delivery electrode 642. Electrical impulse delivery electrode 642 can be made from stainless steel, iridium, platinum or a platinum alloy and may have a round or flat cross-section (not shown). As seen, electrical impulse delivery electrode 642 is a coil wound around tubular section 632, however the ends 643 of electrical impulse delivery electrode 642 partially penetrate tubular section 632. Electrical impulse delivery electrode 642 is used for delivering shocks and electrical impulses to the heart, specifically when the heart experiences an arrhythmia and is thus also positioned on the outer surface of tubular section 632. In one embodiment of the disclosed technique, tip section 634 and first sensing ring 638 may be coupled together to form a single structure, as tip section 634 is made from metal.

A cross-section view of tubular section 632 is delineated by an arrow 652. Cross-section view 652 shows that tubular section 632 has a solid core 633 but also includes a plurality of channels or lumens along the length of tubular section 632. A set of electrical wiring channels 656 enables wiring to be passed through tubular section 632 to couple first and second sensing rings 638 and 640 and electrical impulse delivery electrode 642 with the electrical feed-through (not shown) of a strain relief (not shown). A safety wire channel 654, which is larger in diameter than set of electrical wiring channels 656, enables a safety wire to be passed through tubular section 632. As shown in the interior view of FIG. 9, a wire 646 is coupled with first sensing ring 638, a wire 650 is coupled with second sensing ring 640 and two wires $648_1$ and $648_2$ are coupled with electrical impulse delivery electrode 642, one at its proximal end and the other at its distal end. Each one of wires 646, $648_1$, $648_2$ and 650 is threaded through one of set of electrical wiring channels 656. First sensing ring 638, second sensing ring 640 and ends 643 of electrical impulse delivery electrode 642 partially penetrate tubular section 632 to reach at least one of set of electrical wiring channels 656. Safety wire channel 654 enables a safety wire 644 to be threaded through the length of tubular section 632. Safety wire 644 is coupled at one end to tip section 634. The other end of safety wire 644 is coupled with the end coupler (not shown) of a transition unit (not shown) for securing lead 630 with a flexible device body (not shown). Safety wire 644 is designed to enable tensile strain to be placed on suture eyelet 636 and for any tensile strain placed on lead 630 to be transferred to safety wire 644 and not to be placed on the other elements of lead 630.

Reference is now made to FIG. 10, which is a schematic illustration showing the interior of the medical device structure of FIG. 2, generally referenced 680, constructed and operative in accordance with a further embodiment of the disclosed technique. Medical device structure 680 shows how all the elements described in FIGS. 3-9 are coupled together to form a flexible rechargeable implantable subcutaneous IMD. Medical device structure shows a lead 682 coupled with a transition unit 684. Lead structure 682 is similar to lead 630 (FIG. 9) and transition unit 684 is similar to transition unit 596 (FIG. 8B). Transition unit 684 includes a strain relief 690 and an end coupler 692. End coupler 692 is coupled with a first outer unit which is coupled with sequential outer units, thus forming a flexible device body 686. Flexible device body 686 includes a plurality of inner components (not labeled). Flexible device body 686 is similar to flexible device body 500 (FIG. 7). A set of zigzag dashed lines 688 separates the various sections of medical device structure 680 as not all elements are shown in FIG. 10. A polymer 694 covers the outer surface of flexible device body 686 and an optional additional coating 696 covers polymer 694. Flexible device body 686 is thus completely sealed to liquids due to the metal covering of the outer units and how the outer units are coupled with one another. Lead 682 and transition unit 684 are sealed to liquids based on the materials strain relief 690 and the tubular section (not labeled) of lead 690 are made from, however since these materials are not metal but may be polymer based, lead 682 and transition unit 684 cannot be considered completely sealed to liquids. As shown by an arrow 698, the ends of polymer 694 and additional coating 696 are slightly tapered to match the tapering of strain relief 690, thus transitioning the outer diameter (not labeled) of flexible device body 686 to the outer diameter (not labeled) of lead 682. The couplings of lead 682 to transition unit 684 and transition unit 684 to flexible device body 686 can be executed as described above in FIGS. 6A-6C and 8B. Medical device structure 680 includes a distal and proximal (i.e., posterior and anterior) end. Lead 682 may represent the distal end of medical device structure 680. Another lead (not shown) coupled with another transition unit (not shown), respectively having similar structures to lead 682 and transition unit 684, is also coupled with flexible device body 686, thus forming the full structure of medical device structure 680, as shown above in FIG. 2.

Reference is now made to FIG. 11A, which is a schematic illustration of the medical device structure of FIG. 2 showing various lengths for the posterior lead, generally referenced 740, constructed and operative in accordance with another embodiment of the disclosed technique. Medical device structure 740 includes an anterior end 742, a posterior end 744 and a flexible device body 748. In the case of medical device structure 740 being a subcutaneous ICD, anterior end 742 is placed anterior to the heart, substantially near the sternum of a patient. Posterior end 744 is placed posterior to the heart, substantially in the back of the patient. Medical device structure 740 is a unitary single structure. In order to accommodate a variety of patient sizes, such as for children, tall people, obese people and the like, medical device structure 740 can be constructed having various lengths. In general, medical device structure 740 will have the same length flexible device body 748 and anterior end 742. However posterior end 744 may vary in length depending on the size and body type of the patient. As shown in FIG. 11A, posterior end 744 can vary from a short lead 746A, to a medium lead 746B, to a long lead 746C. Short lead 746A, medium lead 746B and long lead 746C also show the flexibility of posterior end 744. In general, the variation in length of the leads will be in a tubular section 745 of the leads and not in a function section 747 of the leads.

Reference is now made to FIG. 11B, which is a schematic illustration of the interior of an end coupler, strain relief and lead of the medical device structure of FIG. 2 in which the lead is detachable, generally referenced 770, constructed and operative in accordance with a further embodiment of the disclosed technique. As shown, a transition unit 774 includes a strain relief 776 and an end coupler 778. Strain relief 776 includes a charging coil 792 and end coupler includes an electrical feed-through 788. Strain relief 776, like strain relief 554 (FIG. 8A), is hollow, however a distal end (not labeled) of strain relief 776 includes a female plug 784. Female plug may include a wire box 786 for coupling female plug with electrical feed-through 788. As shown, charging coil 792 is also coupled with electrical feed-through 788. A detachable lead 772 includes a male plug 780 and a wire box 782, for coupling wires in detachable lead 772, such as wires from a sensing ring (not shown) or from an electrical impulse delivery electrode (not shown), with male plug 780. Detachable lead 772 includes a lock (not shown) for securing itself with transition unit 774 and preventing unintentional detachment. The lock may be a set screw, a cam and the like, for securing the detachable lead to the transition unit.

As shown by an arrow 790, male plug 780 fits into female plug 784. In this embodiment of the disclosed technique, a subcutaneous IMD device structure is provided in which at least one lead is detachable from a flexible device body (not shown). Other types of connectors can be used to couple detachable lead 772 with transition unit 774, this being a matter of design choice. In this embodiment, a single flexible device body can be used with different types of detachable leads for different types of uses in a patient. In addition, a single flexible device body can be constructed for a particular type of use and different length detachable flexible leads can then be coupled with the flexible device body depending on the size and build of the patient. For example, the flexible device body may be an ICD device body and different length detachable flexible leads can be coupled with the flexible device body depending on whether the ICD is to be used on a child or a very tall adult.

Figure 1B:
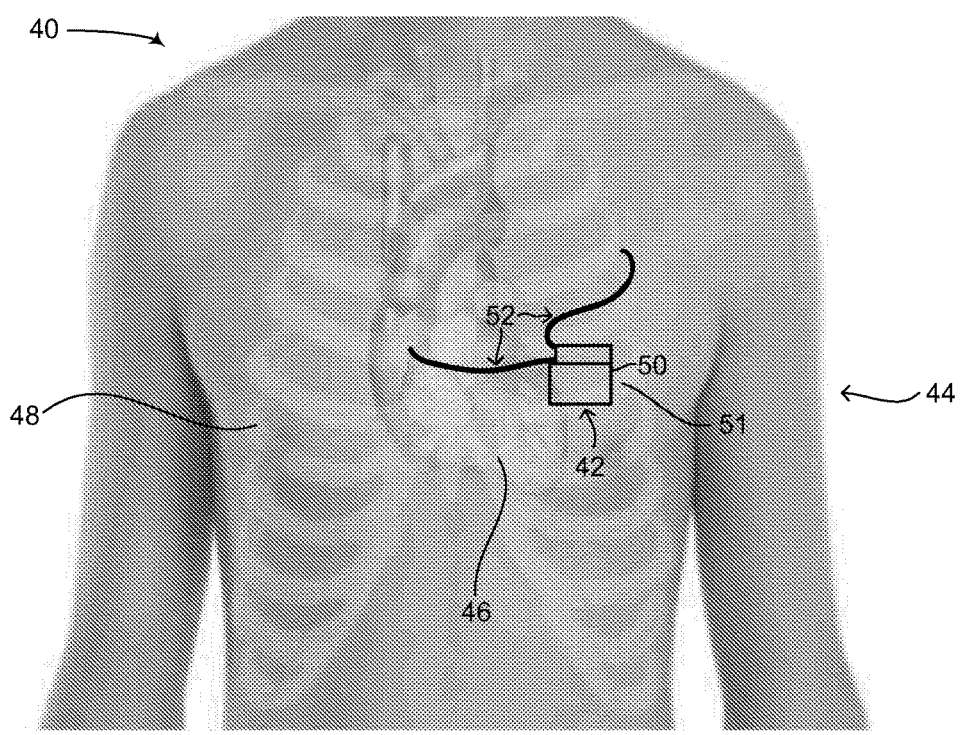
FIG. 1B is a schematic illustration of a subcutaneous ICD implanted in a patient, as is known in the art.
Figure 1C:
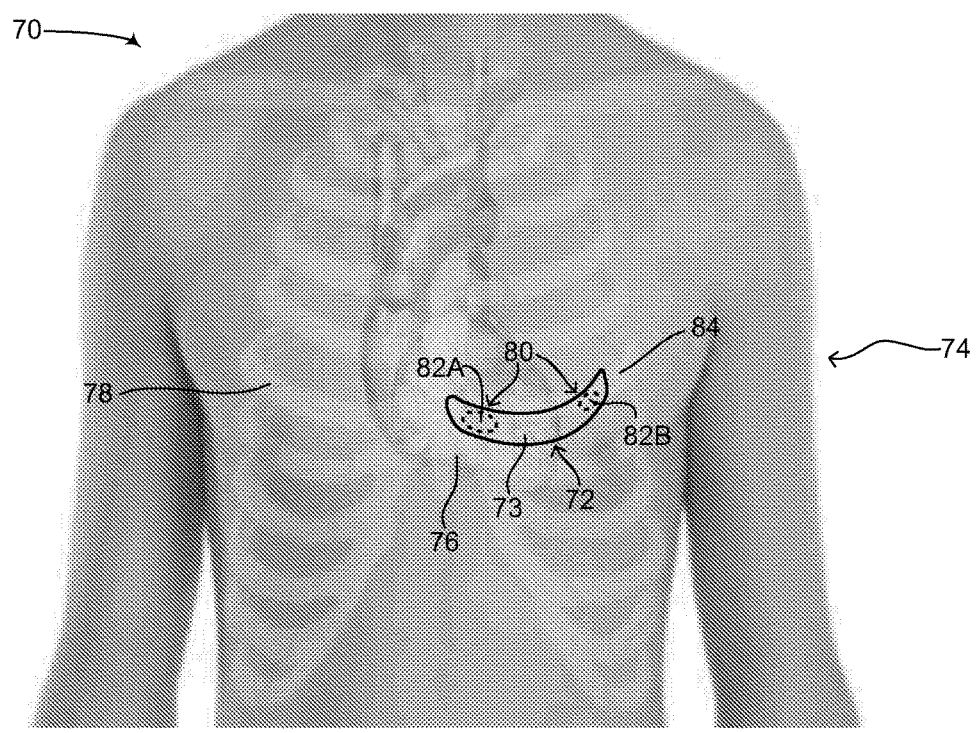
FIG. 1C is a schematic illustration of another subcutaneous ICD implanted in a patient, as is known in the art.
Figure 12:
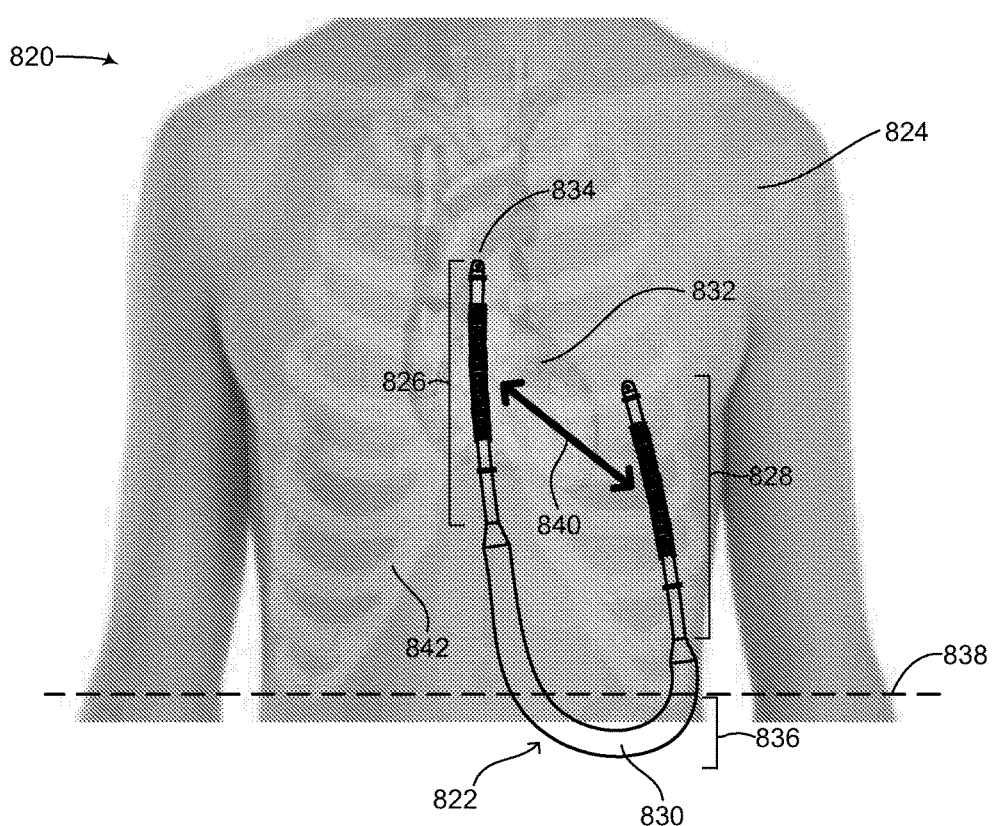
FIG. 12 is a schematic illustration of the medical device structure of FIG. 2 implanted in a patient, constructed and operative in accordance with another embodiment of the disclosed technique.

Reference is now made to FIG. 12, which is a schematic illustration of the medical device structure of FIG. 2 implanted in a patient, generally referenced 820, constructed and operative in accordance with another embodiment of the disclosed technique. As shown, a medical device structure 822, embodied as a subcutaneous ICD, includes a flexible anterior lead 826, a flexible posterior lead 828 and a flexible device body 830, similar to the medical device structure shown above in FIG. 2. FIG. 12 shows how medical device structure 822 is positioned in the body of a patient 824 around a heart 832. In addition, FIG. 12 shows how the placement of medical device structure 822 is different than the placement of prior art ICDs as shown above in FIGS. 1A-1C.

Medical device structure 822 is positioned around heart 832. Flexible anterior lead 826 is substantially positioned over or near a sternum 834 of the patient, whereas flexible posterior lead 828 is positioned in the back of the patient. Flexible anterior lead 826 may be positioned along one side of sternum 834. Flexible device body 830 which couples the two leads together is placed below a ribcage 842 of patient 824, substantially following the outer perimeter of ribcage 842 from the anterior to the posterior of patient 824. Thus besides flexible anterior lead 826 which is positioned over or near sternum 834, no part of medical device structure 822 is actually placed over ribcage 842. A dotted line 838 denotes the divide between the thoracic region and the abdominal region of patient 824. As shown, a substantial portion of medical device structure 822 is situated subcutaneously in the thoracic region of patient 824, however a sizeable portion of medical device structure 822 is also located subcutaneously in the abdominal region of patient 824, denoted by a line 836. Flexible anterior lead 826 and flexible posterior lead 828 are positioned subcutaneously around heart 832 such that an electric shock vector 840 is formed between the leads.

Figure 13C:
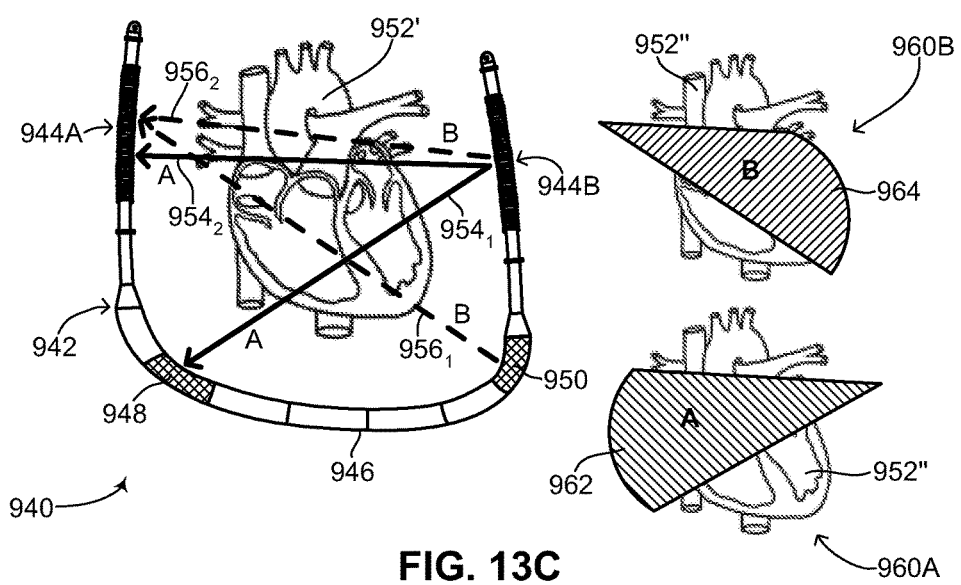
FIG. 13C is a schematic illustration of various possible electric shock vectors using the medical device structure of FIGS. 13A and 13B, constructed and operative in accordance with another embodiment of the disclosed technique.
Figure 13A:
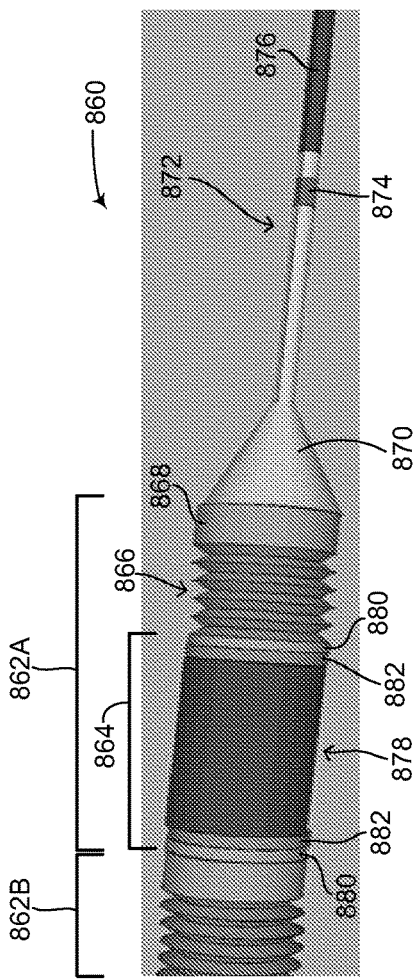
FIGS. 13A and 13B are schematic illustrations of another flexible rechargeable implantable subcutaneous medical device structure, constructed and operative in accordance with a further embodiment of the disclosed technique.
Figure 13B:
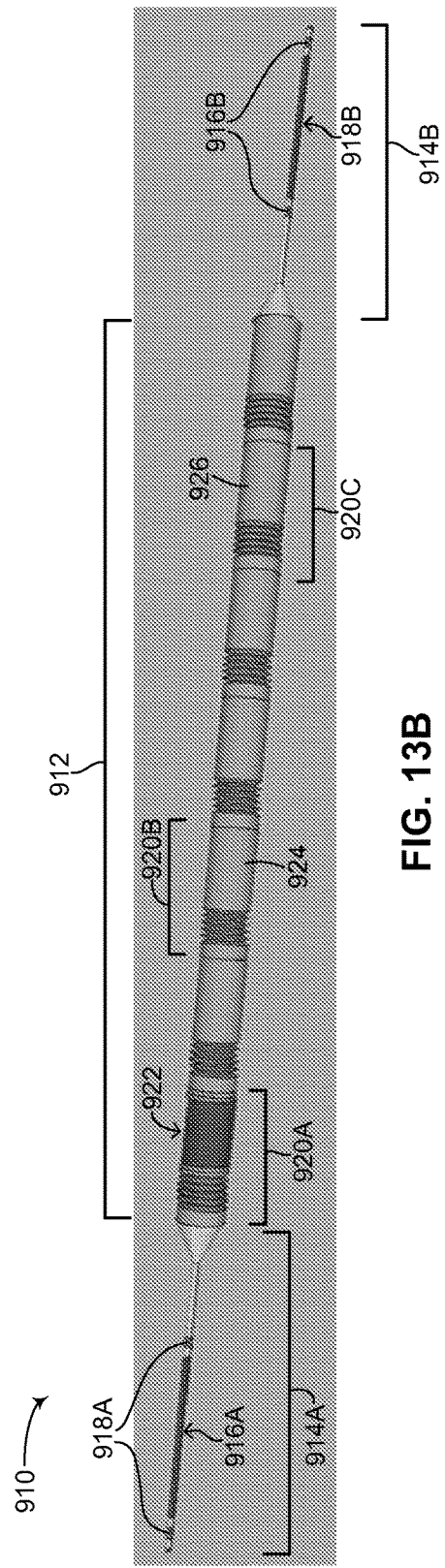

Reference is now made to FIGS. 13A and 13B, which are schematic illustrations of another flexible rechargeable implantable subcutaneous medical device structure, generally referenced 860 and 910 respectively, constructed and operative in accordance with a further embodiment of the disclosed technique. FIG. 13A shows a portion of a subcutaneous medical device structure whereas FIG. 13B shows the entire subcutaneous medical device structure. With reference to FIG. 13A, subcutaneous medical device structure 860 is substantially similar to subcutaneous medical device structure 100 (FIG. 2) and is embodied in FIG. 13A as a subcutaneous ICD. Only a portion of subcutaneous ICD 860 is shown and in addition, the outer surface of the outer units is not shown with a polymer cover or additional coating, as described above in FIG. 7, in order to illustrate the disclosed technique shown in FIG. 13A. Thus, subcutaneous ICD 860 includes at least a polymer cover (not shown) and possibly an additional coating (not shown), however both of these are not shown.

FIG. 13A shows an end of the device structure of subcutaneous ICD 860, including a first outer unit 862A, a second outer unit 862B (which is only partially shown), a transition unit 870 and a lead 872. Lead 872 includes at least one sensing ring 874 and an electrical shock delivery electrode 876. As described above in FIG. 4A, first outer unit 862A includes a first rigid element 864, a second rigid element 868 and a flexible element 866. Flexible element 866 can be embodied as any of the flexible elements shown above in FIG. 4B. First outer unit 862A and in particular first rigid element 864 differ from the first rigid element and outer units described above, for example in FIGS. 4A-4D, in that first rigid element 864 is electrically active. As shown, first rigid element 864 includes an active segment 878, flanked on each side by an isolating ring 882. Each isolating ring 882 is flanked by a non-active ring 880. Active segment 878 is electrically active and is coupled with at least one inner component (not shown) of first outer unit 862A, such as electronics, a battery and/or a high voltage capacitor (all not shown). Alternatively, active element 878 may be coupled with electrical shock delivery electrode 876 directly. Other coupling configurations of active segment 878 are also possible and are a matter of design choice. Active segment 878 includes only the metal forming a part of first rigid element 864.

Active segment 878 may be made from platinum, titanium, stainless steel or other strong, conductive metals. Isolating rings 882 may be made from glass or other known electrically insulating materials. For example, isolating rings 882 may each be made from alumina which is brazed with gold to active segment 878, which may be made from titanium. Non-active rings 880 may be made from the same material as active segment 878, however non-active rings 880 are not electrically active. As shown in FIG. 13A, active segment 878 is located on a proximal or distal outer unit. In other embodiments of the disclosed technique, it is possible to position the active segment in any of the outer units of subcutaneous ICD 860. In addition, it is also possible to have more than one outer unit include an active segment. FIG. 13C below shows an embodiment in which two different outer units each includes an active segment, however other numbers of outer units with active segments are possible. Even in the case where each outer unit includes an active segment, the active segment of each outer unit is separated by a set of isolating rings and non-active rings, besides the flexible element and second rigid element of each outer unit which are not electrically active. It is noted that active segment 878 is not coated or covered by a polymer or sheath, unlike the rest of subcutaneous ICD 860 which is covered or coated (not shown).

In the embodiment of FIG. 13A, since active segment 878 is electrically active, besides electrical shock delivery electrode 876 and the electrical shock delivery electrode (not shown) at the other end of subcutaneous ICD 860, various electrical shock vectors for defibrillating a heart (not shown) are possible. In one embodiment of the disclosed technique, if active segment 878 is positioned at a distal or proximal end of the device body (not labeled) of subcutaneous ICD 860, then it may be electrically coupled with the electrical shock delivery electrode adjacent to it (not shown). Subcutaneous ICD 860 can thus deliver an electrical shock vector between its two electrical shock delivery electrodes or between one of its electrical shock delivery electrodes and active segment 878, thus generating different electrical shock vectors. It is noted that active segment 878 can also function as an additional sensing ring in order to sense electrocardiogram data in parallel to its ability to deliver an electric shock vector. Since active segment 878 is part of the flexible device body (not labeled) of subcutaneous ICD 860 and not part of lead 872, the electrically active surface area of active segment 878 may be larger than the electrically active surface area of electrical shock delivery electrode 876. For example, if electrical shock delivery electrode 876 is 15 centimeters (herein abbreviated cm) in length with an outer diameter of 3 millimeters (herein abbreviated mm), its electrically active surface area is approximately 1414 $mm^2$, whereas if active segment 878 is 4 cm in length with an outer diameter of 13 mm, its electrically active surface area is approximately 1634 $mm^2$. In another embodiment of the disclosed technique, the dimensions of subcutaneous ICD 860 may be determined such that the active surface area of electrical shock delivery electrode 867 is substantially equal to the active surface area of active segment 878.

With reference to FIG. 13B, a subcutaneous medical device structure 910 is shown which is substantially similar to subcutaneous medical device structure 100 (FIG. 2). Subcutaneous medical device structure 910 can be embodied as a subcutaneous ICD and is substantially similar to subcutaneous ICD 860 (FIG. 13A), except the entire device of FIG. 13A is now visible besides its outer sheath. As shown, subcutaneous ICD 910 includes a flexible device body 912, a proximal lead 914A and a distal lead 914B. Proximal lead 914A includes an electrical shock delivery electrode 916A which is flanked on either side by a plurality of sensing rings 918A. In the embodiment shown, one sensing rings is on each side of electrical shock delivery electrode 916A. Similarly, distal lead 914B includes an electrical shock delivery electrode 916B which is flanked on either side by a plurality of sensing rings 918B. As in FIG. 13A, subcutaneous ICD 910 is shown without a polymer cover, sheath or additional coating, however subcutaneous ICD 910 does include a polymer cover or sheath (both not shown) and optionally an additional coating (not shown) as well. Such coating or sheath covers the whole device except for the active segment which remains exposed as well as the leads.

As shown, flexible device body 912 includes seven outer units. Three of the outer units have been labeled as 920A, 920B and 920C. In the embodiment shown in FIG. 13B, only outer unit 920A includes an active segment 922, as was described above in FIG. 13A. Outer unit 920A may contain a battery, thus simplifying the coupling between active segment 922 and at least one inner component (not shown) in flexible device body 912, as the active segment is coupled with the inner component it contains. However, active segment may also be coupled with an inner component located in another outer unit. In another embodiment (not shown), other outer units in flexible device body 912 may include active segments (not specifically shown). For example, outer unit 920B may include an active segment 924 and outer unit 920C may include an active segment 926.

Reference is now made to FIG. 13C, which is a schematic illustration of various possible electric shock vectors using the subcutaneous medical device structures of FIGS. 13A and 13B, generally referenced 940, constructed and operative in accordance with another embodiment of the disclosed technique. FIG. 13C shows a subcutaneous ICD 942, substantially similar to the subcutaneous medical device structures shown in FIGS. 13A and 13B. For the purpose of clarity not all components of subcutaneous ICD 942 are labeled. Subcutaneous ICD 942 includes a flexible device body 946, a proximal electrical shock delivery electrode 944A and a distal electrical shock delivery electrode 944B. Flexible device body 946 includes seven outer units. Two of the seven outer units include active segments, schematically shown as first active segment 948 and second active segment 950. First active segment 948 is not located in an end outer unit whereas second active segment 950 is located at the distal end outer unit (not labeled) of flexible device body 946. The selected outer units with active segments and the number of active segments shown are merely illustrative. In the embodiment shown in FIG. 13C, more than two outer units may include active segments and the active segments may be positioned in any of the outer units of flexible device body 946.

In the embodiment shown in FIG. 13C, subcutaneous ICD 942 is positioned around a heart 952' for delivering electrical shock vectors for treating various arrhythmias. First and second active segments 948 and 950 can be dynamically coupled with proximal electrical shock delivery electrode 944A and distal electrical shock delivery electrode 944B, thus enabling various electrical shock vectors through heart 952'. FIG. 13C shows two possible electrical shock vector configurations, denoted as 'A' and 'B'. Other electrical shock vector configurations in FIG. 13C are also possible (not shown) and understood by the worker skilled in the art. In electrical shock vector configuration A, active segment 948 is selected and an electric shock vector is provided through heart 952' from distal electrical shock delivery electrode 944B to both active segment 948, as shown by a shock vector 954$_1$, and proximal electrical shock delivery electrode 944A, as shown by a shock vector 954$_2$. In electrical shock vector configuration B, active segment 950 is selected and an electric shock vector is provided through heart 952' from both active segment 950 and distal electrical shock delivery electrode 944B to proximal electrical shock delivery electrode 944A, respectively shown by a shock vector 956$_1$ and a shock vector 956$_2$. When an active segment is selected, it is electrically coupled with at least one inner component (not shown), at least one electrical shock delivery electrode or both.

The dynamical coupling of the active segments of subcutaneous ICD 942 can be programmed by a physician and may enable improved treatment of arrhythmias by enabling different parts of the heart to be treated with electrical shocks, depending on which active segment or segments are selected. This is shown in FIG. 13C in two schematic illustrations as indicated by a set of arrows 960A and 960B. Illustration 960A shows the electrical shock vector 962 produced via electrical shock vector configuration A through a heart 952". Illustration 960B shows the electrical shock vector 964 produced via electrical shock vector configuration B through heart 952". As can be seen, electrical shock vector 962 and electrical shock vector 964 cover different areas of heart 952" and thus enable different areas of heart 952" to be treated with electrical impulses or shocks. As mentioned above, other electrical shock vector configurations are possible, including those where more than one active segment is selected.

Figure 14A:
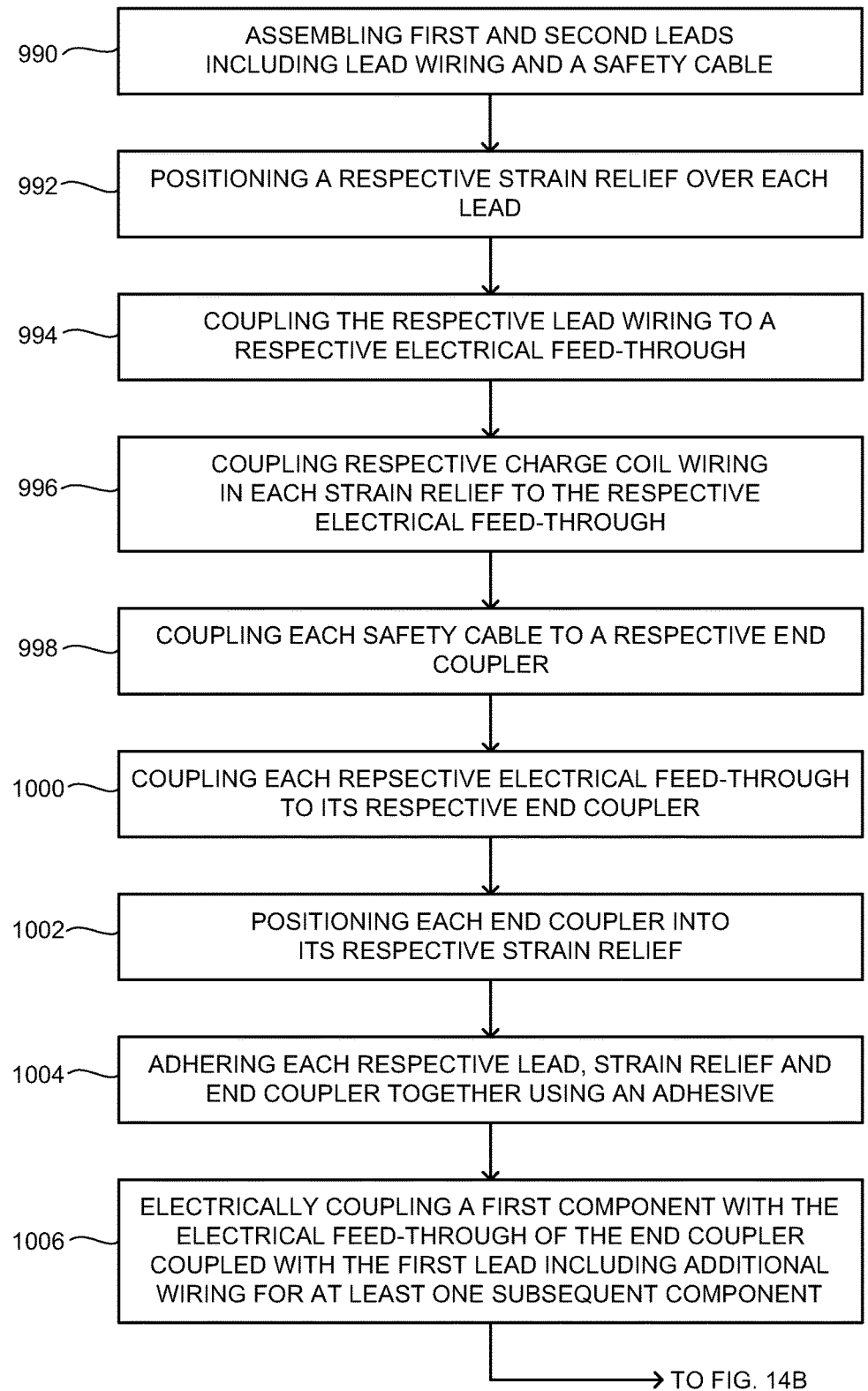
FIGS. 14A-14C are schematic illustrations showing a method of assembly of the medical device structure of FIG. 2, operative in accordance with a further embodiment of the disclosed technique.
Figure 14B:
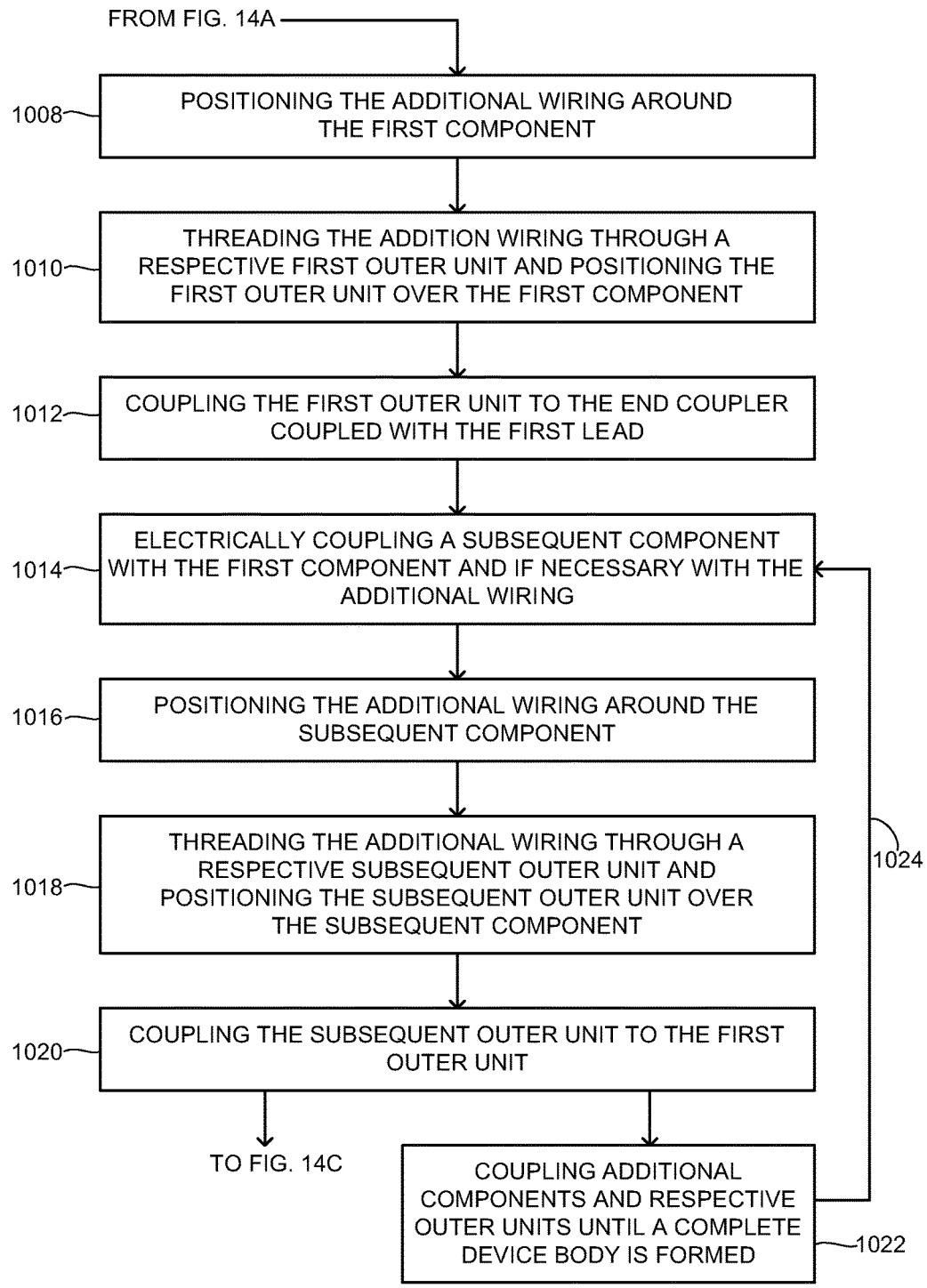
Figure 14C:
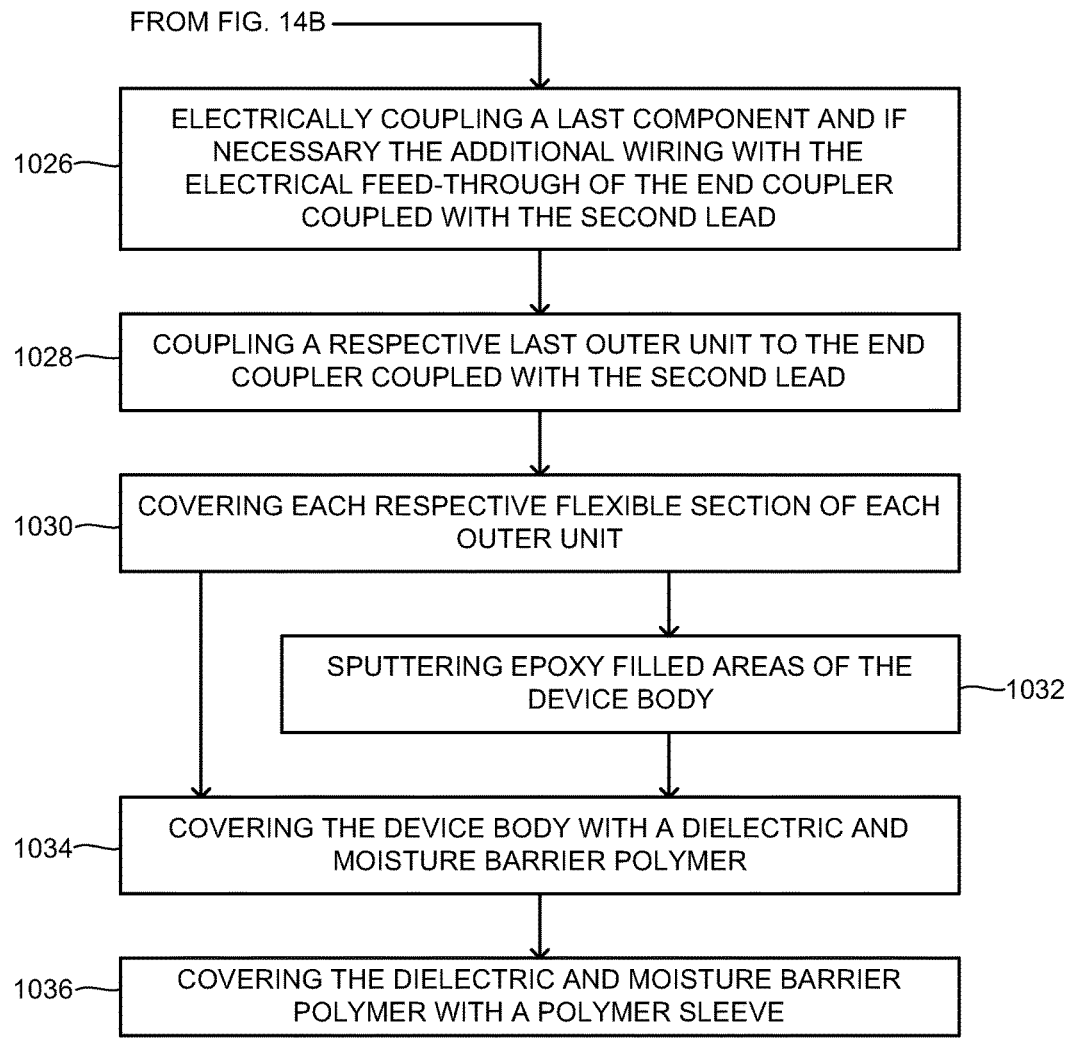

Reference is now made to FIGS. 14A-14C, which are schematic illustrations showing a method of assembly of the medical device structure of FIG. 2, operative in accordance with another embodiment of the disclosed technique. With reference to FIG. 14A, in a procedure 990, first and second leads are assembled. This includes lead wiring and a safety cable, as described above in FIG. 9. Each lead is assembled including its tip section, at least one sensing ring and electrical shock delivery electrode. Lead wiring for coupling the at least one sensing ring and the electrical shock delivery electrode is threaded through wiring channels in the tubular section of the lead. The safety cable is also threaded through a wire channel in the tubular section and coupled with the tip section. With reference to FIG. 9, a wire 646 (FIG. 9) is coupled with first sensing ring 638 (FIG. 9), a wire 650 (FIG. 9) is coupled with second sensing ring 640 (FIG. 9) and two wires 648₁ and 648₂ (both from FIG. 9) are coupled with electrical impulse delivery electrode 642 (FIG. 9), one at its proximal end and the other at its distal end. Each one of wires 646, 648₁, 648₂ and 650 is threaded through one of set of electrical wiring channels 656 (FIG. 9). Safety wire channel 654 (FIG. 9) enables a safety wire 644 (FIG. 9) to be threaded through the length of tubular section 632 (FIG. 9). Safety wire 644 is coupled at one end to tip section 634 (FIG. 9). After procedure 990, a first lead and a second lead are fully assembled as shown in FIG. 9.

In a procedure 992, a respective strain relief is positioned over each lead. Each strain relief is positioned over the tubular section of a respective lead and includes a charge coil. With reference to FIG. 8A, strain relief 554 (FIG. 8A) also includes a charging coil 562 (FIG. 8A) which is coupled with electrical feed-through 556 (FIG. 8A) via a plurality of wires. In a procedure 994, the respective lead wiring of a lead is coupled to a respective electrical feed-through. As mentioned above, this includes lead wiring coupling at least one sensing ring and an electrical impulse or shock delivery electrode. Lead wiring is coupled usually by soldering or electrically coupling the lead wiring to electrical connectors on the electrical feed-through. With reference to FIG. 8A, a plurality of sensing wires 568 (FIG. 8A), coupled with sensors or sensing rings in lead 564 (FIG. 8A) are coupled with plurality of connectors 558 (FIG. 8A) in electrical feed-through 556. In a procedure 996, respective charge coil wiring in each strain relief is coupled to the respective electrical feed-through. With reference to FIG. 8B, charging coil 610 (FIG. 8B) is coupled with a plurality of wires 612 (FIG. 8B) to connectors in electrical feed-through 602 (FIG. 8B).

+++In a procedure 998, each safety cable is coupled to a respective end coupler. With reference to FIG. 8A, safety wire 566 (FIG. 8A), running through lead 564 (FIG. 8A), is also coupled with electrical feed-through 556 (FIG. 8A) and is used for securing lead 564 (FIG. 8A) to the flexible device body via end coupler 552 (FIG. 8A), for preventing lead 564 from detaching from the flexible device body. In a procedure 1000, each respective electrical feed-through is coupled, for example by welding or by the use of an adhesive, to its respective end coupler. With reference to FIG. 8A, electrical feed-through 556 may be constructed as a separate part which can be coupled to end coupler 552, for example by a weld, by an adhesive and the like. In a procedure 1002, each end coupler is positioned into its respective strain relief and in a procedure 1004, each respective lead, strain relief and end coupler is adhered together using an adhesive. With reference to FIG. 8A, lead 564 is coupled with strain relief 554 (FIG. 8A) via an adhesive, such as silicone or polyurethane. Flat end 557 (FIG. 8A) is shaped to fit into one end of end coupler 552 and may be coupled with end coupler 552 via an adhesive 560 (FIG. 8A). As described above, procedures 992 to 1004 result in the assembly of a transition unit as shown above in FIG. 8A. The major components of the transition unit, such as a strain relief, an end coupler and an electrical feed-through are separate components which are electrically and mechanically coupled to a respective lead as described in the above procedures. In an alternative procedure to procedure 1004, each respective strain relief and end coupler is adhered together using an adhesive while each respective lead is coupled with its respective strain relief. The lead in this alternative procedure may be a detachable lead having a male plug which couples with a female plug in the strain relief. A lock may be engaged to prevent the detachable lead from accidentally detaching from the strain relief. An example of this was shown above in FIG. 11B.

In a procedure 1006, a first component is electrically coupled with the electrical feed-through of the end coupler coupled with the first lead, including additional wiring for at least one subsequent component. The first component can be any inner component as described above in FIG. 3, such as a battery, a capacitor or electronics. In this procedure, the first component is electrically coupled with at least one of the connectors on the other side of the electrical feed-through. Additional wiring for coupling at least one subsequent component with the electrical feed-through is also electrically coupled with the electrical feed-through. With reference to FIG. 8B, epoxy 606 (FIG. 8B) also couples inner component 594 (FIG. 8B) to outer unit 592 (FIG. 8B) and secures a plurality of wires 614 (FIG. 8B). Charging coil 610 (FIG. 8B) is coupled with a plurality of wires 612 (FIG. 8B) to connectors in electrical feed-through 602 (FIG. 8B). Plurality of wires 612 is coupled via electrical feed-through 602 to plurality of wires 614, which couples charging coil 610 with a plurality of batteries.

With reference to FIG. 14B, in a procedure 1008, the additional wiring is positioned around the first component, as shown in FIGS. 3 and 5. With reference to FIG. 5, a wire 348A (FIG. 5) electrically couples first inner component 344A (FIG. 5) with another inner component or element, such as a sensing ring or an electrical impulse delivery electrode, whereas a wire 348B (FIG. 5) runs along the length of the inner components yet is coupled with none of them. In a procedure 1010, the addition wiring is threaded through a respective first outer unit and the first outer unit is positioned over the first component. It is noted that the first outer unit is already assembled, including a first rigid element, a flexible element and a second rigid element. The first outer unit can be any of the outer units described above, such as in FIGS. 4A and 4B. With reference to FIG. 5, a first inner component 344A is placed inside first outer unit 342A (FIG. 5) and a second inner component 344B (FIG. 5) is placed inside second outer unit 342B (FIG. 5). In a procedure 1012, the first outer unit is coupled to the end coupler coupled with the first lead. As described above in FIG. 8B, the coupling between the first outer unit and the end coupler can be via welding, soldering or via the use of an epoxy. With reference to FIG. 8B, outer unit 592 (FIG. 8B) is positioned adjacent to end coupler 598 (FIG. 8B) however a gap 604 (FIG. 8B) is present between the two elements. Gap 604 is filled with an epoxy 606 (FIG. 8B). Epoxy 606 substantially couples end coupler 598 and outer unit 592 together. Epoxy 606 also couples inner component 594 (FIG. 8B) to outer unit 592 and secures a plurality of wires 614 (FIG. 8B). In another embodiment of the disclosed technique, end coupler 598 and outer unit 592 can be welded or soldered together. In a further embodiment of the disclosed technique, outer unit 592 may be coupled with end coupler 598 via a flexible element.

In a procedure 1014, a subsequent component is electrically coupled with the first component and if necessary with the additional wiring. As mentioned above in procedure 1006 (FIG. 14A), the component referred to in procedure 1014 refers to an inner component, such as a battery, capacitor or electronics. With reference to FIG. 3, inner components 150 (FIG. 3) are coupled with one another via electrical wires, such as plurality of wires 158 (FIG. 3) and 162 (FIG. 3). Wires connecting adjacent components may be placed in the space between components, such as gap 170 (FIG. 3), with ample slack to enable sufficient bending between adjacent components. Wires not connecting adjacent components are run on the outer surface of components or within manufactured grooves or recesses on the outer surface of components. In a procedure 1016, the additional wiring is positioned around the subsequent component, similar to procedure 1008. In a procedure 1018, the additional wiring is threaded through a respective subsequent outer unit and the subsequent outer unit is positioned over the subsequent component, similar to procedure 1010. In a procedure 1020, the subsequent outer unit is coupled to the first outer unit, similar to the coupling between the first outer unit and the end coupler coupled with the first lead, similarly as mentioned above in procedure 1012. As mentioned above, the coupling between outer units can be either via welding, soldering or via the use of an epoxy, as described above in FIG. 5. In a procedure 1022, additional components and respective outer units are coupled until a complete device body is formed. As shown, after procedure 1022, the method of assembly returns to procedure 1014, shown by an arrow 1024. Procedures 1014 to 1020 are repeated as additional inner components and outer units are assembled, thus resulting in a complete device body, for example, as shown in FIG. 4D. Once the device body has been completely assembled, procedure 1020 proceeds to procedure 1026 (FIG. 14C).

Procedures 1006 (FIG. 14A) to 1022 describe how a device body of the disclosed technique is assembled, substantially from one side of the device body to the other. As described above, the device body is assembled piece by piece from one transition unit to the other transition unit. In an alternative to procedures 1006 to 1022, after procedure 1004 (FIG. 14A), the assembled transition units are placed aside and the device body is assembled as described in procedures 1006 to 1022, however assembly begins in the middle of the device body and grows outwards towards each transition unit. For example, as shown above in FIG. 3, electronics 152 (FIG. 3) may be assembled in its outer unit first, and then a plurality of batteries are assembled to one side of electronics 152 whereas a plurality of capacitors are assembled to the other side of electronics 152, as per the device structure shown in FIG. 3. Once the device body has been assembled, procedures 1026 and 1028 (as described below in FIG. 14C) are executed on both transition units to each side of the device body, thereby coupling the transition units to the device body on each side.

With reference to FIG. 14C, in a procedure 1026, a last component is electrically coupled and if necessary, the additional wiring as well, with the electrical feed-through of the end coupler coupled with the second lead. This is similar to procedure 1006 (FIG. 14A). As described above, even though both leads were assembled in procedure 990 (FIG. 14A), the second lead is only attached to the device body once the device body has been completely assembled. In a procedure 1028, a respective last outer unit is coupled to the end coupler coupled with the second lead. This is similar to procedure 1012 (FIG. 14B). At this point in the method of assembly, the medical device structure has been fully assembled. However, the medical device structure still requires a number of coatings and coverings before being complete, which are described in procedures 1030 to 1036.

In a procedure 1030, each respective flexible section of each outer unit is covered. As described above in FIGS. 4A-4B, each outer unit includes a flexible element. In FIGS. 6A-6C, various coverings are shown for covering the flexible elements in the various outer units shown in FIGS. 4A-4B. In this procedure, the flexible sections may be covered with a polymer or a thin metal covering. With reference to FIG. 6A, flexible element 398 (FIG. 6A) is covered by a polymer 400 (FIG. 6A), which substantially fills in the bends and folds of plurality of pleats 399 (FIG. 6A) of flexible element 398. With reference to FIG. 6B, flexible element 428 (FIG. 6B) is covered by a thin metal covering 436 (FIG. 6B), which substantially covers flexible element 428. With reference to FIG. 6C, second outer unit 462B (FIG. 6C) includes a flexible element 468 (FIG. 6C), which has an hourglass shape. The hourglass shape of flexible element 468 creates a cavity 472 (FIG. 6C) in which bodily tissue growth can occur. Cavity 472 is filled in using a polymer 474 (FIG. 6C). In a procedure 1032, epoxy filled areas of the completed device body are sputtered. Procedure 1032 is only executed if the outer units are coupled together by an epoxy in procedures 1012, 1020 (both from FIG. 14B) and 1028. In such a case, the epoxy filled areas are covered by a sputtered metal. The method then proceeds to a procedure 1034. With reference to FIG. 5, once epoxy 360 (FIG. 5) is dry, the exterior surface of epoxy 360, which couples first outer unit 342A (FIG. 5) with second outer unit 342B (FIG. 5) is covered by a thin layer 362 (FIG. 5). Thin layer 362 may be a thin metal layer, such as platinum, stainless steel, titanium or gold, which is sputtered over the exterior surface of epoxy 360. Thin layer 362 may also be a metal-filled epoxy.

In the case that the outer units are coupled together via welding, brazing or soldering, immediately after executing procedure 1030, procedure 1034 is executed. In procedure 1034, the complete device body is covered with a dielectric and moisture barrier polymer. With reference to FIG. 7, once all inner components and outer units have been coupled together, the outer surface of the outer units, i.e., outer surface 517 (FIG. 7) of flexible device body 500 (FIG. 7), may be coated or covered with a polymer 518 (FIG. 7). Polymer 518 may be a poly(para-xylylene) polymer, such as Parylene. Polymer 518 may be any biocompatible, liquid resistant polymer. In a procedure 1036, the dielectric and moisture barrier polymer is covered with a polymer sleeve. It is noted that procedure 1036 is optional. With reference to FIG. 7, optionally, an addition coating 520 (FIG. 7) may be placed over polymer 518. Addition coating 520 may be a polymer sleeve made from a chemically inert material, such as PTFE, ePTFE, or from materials such as ETFE, for preventing bodily tissue growth on the outer surface of flexible device body 500 and for easing in the removal of flexible device body 500 from a patient. After procedure 1036, the complete device body is assembled as seen in FIG. 7, and the entire medical device structure is as shown in FIGS. 2 and 10.

It will be appreciated by persons skilled in the art that the disclosed technique is not limited to what has been particularly shown and described hereinabove. Rather the scope of the disclosed technique is defined only by the claims, which follow.

The invention claimed is:

1. Flexible subcutaneous implantable cardioverter defibrillator (ICD) for regulating arrhythmias in a heart of a patient, comprising:
   a flexible device body;
   at least one flexible lead; and
   at least one respective transition unit, for respectively coupling each one of said at least one flexible lead to said flexible device body,
   said flexible device body comprising:
      a plurality of inner components; and
      a respective plurality of hollow outer units, for encasing and protecting said plurality of inner components,
      said plurality of inner components comprising at least one high voltage capacitor,
      each one of said plurality of hollow outer units comprising:

at least one hollow rigid element; and
a hollow flexible element, coupled with said at least one hollow rigid element, for enabling said outer unit a degree of flexibility,
wherein said hollow flexible element is covered with a covering,
said at least one respective transition unit comprising:
an end coupler; and
a strain relief,
said end coupler comprising an electrical feed-through, for enabling wiring interior to said flexible device body to be coupled with wiring exterior to said flexible device body in a liquid-proof manner, and
said strain relief comprising a charging coil, for recharging a rechargeable power source in said flexible device body,
wherein said flexible device body is covered with a polymer for preventing bodily tissue growth on an outer surface of said flexible device body;
wherein said flexible subcutaneous ICD is completely positioned subcutaneously, superficially placed under the skin of said patient, when in operation; and
wherein said at least one high voltage capacitor can store at least 3.5 joules per cubic centimeter (J/cc) of energy.

2. The flexible subcutaneous ICD according to claim 1, wherein said flexible device body is hermetically sealed.

3. The flexible subcutaneous ICD according to claim 1, wherein a cross-section of said flexible device body is symmetric.

4. The flexible subcutaneous ICD according to claim 1, said at least one flexible lead comprising:
a tubular section;
an electrical impulse delivery electrode, for providing at least one of a low voltage electrical shock and a high voltage electrical shock to said heart in said patient;
at least one sensing ring, for detecting electrical activity of said heart in said patient and for providing detected electrical activity to electronics in said flexible device body;
a tip section; and
a suture eyelet.

5. The flexible subcutaneous ICD according to claim 4, said tubular section further comprising at least one hollow channel, wherein said electrical impulse delivery electrode is coupled with a wire through said at least one hollow channel with said at least one respective transition unit.

6. The flexible subcutaneous ICD according to claim 1, wherein said flexible device body has a first diameter and said at least one flexible lead has a second diameter, wherein said first diameter and said second diameter are each isodiametric.

7. The flexible subcutaneous ICD according to claim 1, wherein said end coupler is coupled with said hollow flexible element of a given one of said respective plurality of hollow outer units.

8. The flexible subcutaneous ICD according to claim 1, wherein said electrical feed-through is dielectrically shielded, is positioned at a center of said end coupler and shields said end coupler from at least one of electrical interference and magnetic interference.

9. The flexible subcutaneous ICD according to claim 1, said electrical feed-through comprising at least one filter selected from the list consisting of:
a dielectric barrier;
a moisture barrier;
a electromagnetic filter;
a radio-frequency filter;
a hermetic seal;
a discoidal capacitive filter; and
a passive electrical filter, for preventing current spikes from entering said flexible device body.

10. The flexible subcutaneous ICD according to claim 1, wherein said at least one respective transition unit seals said flexible device body from liquid and moisture while simultaneously enabling wiring in said at least one flexible lead to be electrically coupled with wiring in said flexible device body.

11. The flexible subcutaneous ICD according to claim 1, wherein for each one of said plurality of hollow outer units said hollow flexible element is sandwiched between a first one of said at least one hollow rigid element and a second one of said at least one hollow rigid element.

12. The flexible subcutaneous ICD according to claim 1, wherein both said at least one hollow rigid element and said hollow flexible element are cylindrical in shape and have substantially the same diameter.

13. The flexible subcutaneous ICD according to claim 1, wherein said covering is a polymer fill and wherein said polymer fill is a polymer selected from the list consisting of:
silicone,
Parylene,
polyurethane; and
polytetrafluoroethylene (PTFE).

14. The flexible subcutaneous ICD according to claim 1, wherein said covering is a thin metal cover made from a thin metal foil selected from the list consisting of:
a titanium foil;
a gold foil; and
a titanium and gold alloy foil.

15. The flexible subcutaneous ICD according to claim 1, wherein said covering is for providing an exterior surface of said hollow flexible element with a smooth outer surface and for preventing bodily tissue growth in said hollow flexible element.

16. The flexible subcutaneous ICD according to claim 1, wherein said hollow flexible element comprises a bellows shape, said bellows shape comprising a plurality of pleats.

17. The flexible subcutaneous ICD according to claim 1, wherein said hollow flexible element is a ball-and-socket joint, wherein a ball of said ball-and-socket joint is hollow, thereby enabling wiring to be passed there through, wherein said ball-and-socket joint comprises a foil for covering said ball-and-socket joint and wherein a first one and a second one of said plurality of inner components are coupled with a safety cable, for preventing said ball of said ball-and-socket joint from dislocating from a socket of said ball-and-socket joint.

18. The flexible subcutaneous ICD according to claim 1, wherein said hollow flexible element is an hourglass shape, said hourglass shape comprising a cavity.

19. The flexible subcutaneous ICD according to claim 1, wherein a gap exists between a first one and a second one of said respective plurality of hollow outer units and wherein said gap is filled with an epoxy.

20. The flexible subcutaneous ICD according to claim 19, wherein said epoxy is a biocompatible epoxy selected from the list consisting of:
silicone;
polyurethane; and
Hysol®; and
a thermoset epoxy.

21. The flexible subcutaneous ICD according to claim 19, wherein said epoxy filling said gap is covered with a thin layer.

22. The flexible subcutaneous ICD according to claim 21, wherein said thin layer is selected from the list consisting of:
   a thin metal layer; and
   a metal-filled epoxy.

23. The flexible subcutaneous ICD according to claim 21, wherein said thin layer acts as a moisture barrier and as an electromagnetic shield over an exterior surface of said epoxy filling said gap, wherein said epoxy filling said gap and said thin layer couple said first one with said second one of said respective plurality of hollow outer units and wherein said thin layer is partially flexible.

24. The flexible subcutaneous ICD according to claim 1, wherein an interior of said respective plurality of hollow outer units is at least filled partially with a substance selected from the list consisting of:
   a desiccant; and
   an epoxy, for anchoring said plurality of inner components and wiring placed within each one of said respective plurality of hollow outer units.

25. The flexible subcutaneous ICD according to claim 1, wherein a first one and a second one of said respective plurality of hollow outer units are coupled together by a technique selected from the list consisting of:
   welding;
   soldering;
   brazing; and
   use of an adhesive.

26. The flexible subcutaneous ICD according to claim 1, wherein an interior of each one of said respective plurality of hollow outer units is filled with a substance and wherein said substance is a polymer which hardens upon exposure to moisture.

27. The flexible subcutaneous ICD according to claim 1, wherein said polymer is selected from the list consisting of:
   a poly(para-xylylene) polymer;
   Parylene; and
   a biocompatible, liquid resistant polymer.

28. The flexible subcutaneous ICD according to claim 1, wherein said polymer is covered with a coating and wherein said coating is a polymer sleeve made from a chemically inert material.

29. The flexible subcutaneous ICD according to claim 4, said plurality of inner components comprising:
   said rechargeable power source; and
   electronics.

30. The flexible subcutaneous ICD according to claim 29, wherein said at least one high voltage capacitor is for storing said at least one of said low voltage electrical shock and said high voltage electrical shock delivered by said electrical impulse delivery electrode; and
   wherein said rechargeable power source comprises at least one battery for powering said electronics.

31. The flexible subcutaneous ICD according to claim 1, wherein a wiring coupling said plurality of inner components is run on an outer surface of each one of said plurality of inner components.

32. The flexible subcutaneous ICD according to claim 29, said electronics comprising:
   a processor;
   a decision circuit, for receiving signals from said at least one sensing ring, for determining if said detected electrical activity represents a medical problem in said heart in said patient and for deciding what kind of electrical shock should be administered to said heart if said detected electrical activity is determined to represent said medical problem;
   a memory; and
   a transceiver, for transmitting and receiving data.

33. The flexible subcutaneous ICD according to claim 1, wherein said structure is unitary.

34. The flexible subcutaneous ICD according to claim 1, at least one of said respective plurality of hollow outer units comprising an active segment.

35. The flexible subcutaneous ICD according to claim 34, wherein said active segment can receive an electrical shock, can function as a sensing ring and is electrically coupled with at least one of said plurality of inner components and an electrical impulse delivery electrode.

36. The flexible subcutaneous ICD according to claim 1, said structure further comprising at least one sensor for sensing at least one physiological parameter of a patient, said at least one physiological parameter of said patient being selected from the list consisting of:
   transthoracic impedance;
   subcutaneous oxygen;
   pH level;
   glucose level;
   respiratory rate;
   electrical activity of a heart;
   electrical activity of a muscle group;
   a position of said patient;
   an acceleration of said patient; and
   body temperature.

* * * * *